United States Patent
Cabiri et al.

(10) Patent No.: US 10,293,120 B2
(45) Date of Patent: May 21, 2019

(54) REDUNDANT INJECTION DEVICE STATUS INDICATION

(71) Applicant: MEDIMOP Medical Projects Ltd., Ra'anana (IL)

(72) Inventors: Oz Cabiri, Macabim-Reut (IL); Ran Hezkiahu, Herzliya (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 565 days.

(21) Appl. No.: 14/683,193

(22) Filed: Apr. 10, 2015

(65) Prior Publication Data
US 2016/0296716 A1  Oct. 13, 2016

(51) Int. Cl.
*A61M 5/50* (2006.01)
*A61M 5/20* (2006.01)
*A61M 5/32* (2006.01)

(52) U.S. Cl.
CPC ............ *A61M 5/5086* (2013.01); *A61M 5/20* (2013.01); *A61M 5/3202* (2013.01);
(Continued)

(58) Field of Classification Search
CPC .... A61M 2205/3306; A61M 2205/583; A61M 2205/587; A61M 2205/6063; A61M 2205/3379; A61M 5/5086; A61M 2005/2013; A61M 2005/3267; A61M 2205/50; A61M 2205/584;
(Continued)

(56) References Cited

U.S. PATENT DOCUMENTS

| 1,795,630 A | 3/1931 | Wilson |
| 2,860,635 A | 11/1958 | Wilburn |

(Continued)

FOREIGN PATENT DOCUMENTS

| CN | 1747683 A | 3/2006 |
| CN | 1863566 A | 11/2006 |

(Continued)

OTHER PUBLICATIONS

Office Action dated Feb. 20, 2015 in U.S. Appl. No. 13/521,181 by Cabiri.
(Continued)

*Primary Examiner* — Brandy S Lee
(74) *Attorney, Agent, or Firm* — Panitch Schwarze Belisario & Nadel LLP

(57) ABSTRACT

A method and system for a drug delivery device with multiple status indicators is disclosed. For example the device may include an operator indicator and/or second indicator. The indicators may be seen in one location. For example they may be viewed through one optical path. Optionally the operator indicator may attract attention. The operator indicator may give information that is pertinent to operation of the device to an operator of the system. The operator indicator may have an encoded output signal. Optionally a second indicator may convey information that is not conveyed by the user operator by the operator indicator, for example information that is not pertinent to the regular operation of the machine. Alternatively or additional, the second indicator may function at times when operator indicator is not functioning.

18 Claims, 11 Drawing Sheets

(52) U.S. Cl.
CPC .............. *A61M 2005/2013* (2013.01); *A61M 2005/3267* (2013.01); *A61M 2205/3306* (2013.01); *A61M 2205/3379* (2013.01); *A61M 2205/50* (2013.01); *A61M 2205/583* (2013.01); *A61M 2205/584* (2013.01); *A61M 2205/587* (2013.01); *A61M 2205/6063* (2013.01); *A61M 2205/6081* (2013.01)

(58) Field of Classification Search
CPC .. A61M 2205/6081; A61M 5/20; A61M 5/32; A61M 5/3202; A61M 5/508
See application file for complete search history.

(56) References Cited

U.S. PATENT DOCUMENTS

| | | |
|---|---|---|
| 3,203,269 A | 8/1965 | Perrine |
| 3,212,685 A | 10/1965 | Swan et al. |
| 3,794,028 A | 2/1974 | Mueller et al. |
| 3,994,295 A | 11/1976 | Wulff |
| 4,195,636 A | 4/1980 | Behnke |
| 4,218,724 A | 8/1980 | Kaufman |
| 4,273,122 A | 6/1981 | Whitney et al. |
| 4,300,554 A | 11/1981 | Hessberg et al. |
| 4,403,987 A | 9/1983 | Gottinger |
| 4,435,173 A | 3/1984 | Siposs et al. |
| 4,465,478 A | 8/1984 | Sabelman et al. |
| 4,565,543 A | 1/1986 | Bekkering et al. |
| 4,585,439 A | 4/1986 | Michel |
| 4,599,082 A | 7/1986 | Grimard |
| 4,601,702 A | 7/1986 | Hudson |
| 4,685,903 A | 8/1987 | Cable et al. |
| 4,698,055 A | 10/1987 | Sealfon |
| 4,810,215 A | 3/1989 | Kaneko |
| 4,850,966 A | 7/1989 | Grau et al. |
| 4,867,743 A | 9/1989 | Vaillancourt |
| 4,886,499 A | 12/1989 | Cirelli et al. |
| 4,919,596 A | 4/1990 | Slate et al. |
| 4,929,241 A | 5/1990 | Kulli |
| 4,950,246 A | 8/1990 | Muller |
| D322,671 S | 12/1991 | Szwarc |
| 5,109,850 A | 5/1992 | Blanco et al. |
| 5,112,317 A | 5/1992 | Michel |
| 5,131,816 A | 7/1992 | Brown et al. |
| 5,190,521 A | 3/1993 | Hubbard et al. |
| 5,254,096 A | 10/1993 | Rondelet et al. |
| 5,300,045 A | 4/1994 | Plassche, Jr. |
| 5,342,313 A | 8/1994 | Campbell et al. |
| 5,348,544 A | 9/1994 | Sweeney et al. |
| 5,366,498 A | 11/1994 | Brannan et al. |
| 5,383,865 A | 1/1995 | Michel |
| 5,478,315 A | 12/1995 | Brothers et al. |
| 5,482,446 A | 1/1996 | Williamson et al. |
| 5,496,274 A | 3/1996 | Graves et al. |
| 5,501,665 A | 3/1996 | Jhuboo et al. |
| 5,505,709 A | 4/1996 | Funderburk et al. |
| 5,562,686 A | 10/1996 | Sauer et al. |
| 5,593,390 A | 1/1997 | Castellano et al. |
| 5,616,132 A | 4/1997 | Newman |
| 5,643,218 A | 7/1997 | Lynn et al. |
| 5,645,955 A | 7/1997 | Maglica |
| 5,647,853 A | 7/1997 | Feldmann et al. |
| 5,662,678 A | 9/1997 | Macklin |
| 5,672,160 A | 9/1997 | Osterlind et al. |
| 5,690,618 A | 11/1997 | Smith et al. |
| D393,314 S | 4/1998 | Meisner et al. |
| 5,766,186 A | 6/1998 | Faraz et al. |
| 5,795,675 A | 8/1998 | Maglica |
| 5,800,420 A | 9/1998 | Gross et al. |
| 5,807,375 A | 9/1998 | Gross et al. |
| 5,814,020 A | 9/1998 | Gross |
| 5,836,920 A | 11/1998 | Robertson |
| 5,848,991 A | 12/1998 | Gross et al. |
| 5,851,197 A | 12/1998 | Marano et al. |
| 5,858,001 A | 1/1999 | Tsals et al. |
| 5,858,008 A | 1/1999 | Capaccio |
| 5,868,710 A | 2/1999 | Battiato et al. |
| 5,931,814 A | 8/1999 | Alex et al. |
| 5,941,850 A | 8/1999 | Shah et al. |
| 5,948,392 A | 9/1999 | Haslwanter et al. |
| 5,954,697 A | 9/1999 | Srisathapat et al. |
| 5,957,895 A | 9/1999 | Sage et al. |
| 5,968,011 A | 10/1999 | Larsen et al. |
| 5,993,423 A | 11/1999 | Choi |
| 6,004,297 A | 12/1999 | Steenfeldt-Jensen et al. |
| 6,033,245 A | 3/2000 | Yamkovoy |
| 6,033,377 A | 3/2000 | Rasmussen et al. |
| 6,064,797 A | 5/2000 | Crittendon et al. |
| 6,074,369 A | 6/2000 | Sage et al. |
| 6,186,982 B1 | 2/2001 | Gross et al. |
| 6,200,289 B1 | 3/2001 | Hochman et al. |
| 6,200,296 B1 | 3/2001 | Dibiasi et al. |
| 6,224,569 B1 | 5/2001 | Brimhall |
| 6,248,093 B1 | 6/2001 | Moberg |
| 6,277,095 B1 | 8/2001 | Kriesel et al. |
| 6,277,098 B1 | 8/2001 | Klitmose et al. |
| 6,277,099 B1 | 8/2001 | Strowe et al. |
| 6,287,283 B1 | 9/2001 | Ljunggreen et al. |
| 6,293,925 B1 | 9/2001 | Safabash et al. |
| 6,302,633 B1 | 10/2001 | Poe |
| 6,336,729 B1 | 1/2002 | Pavelle et al. |
| 6,345,968 B1 | 2/2002 | Shupe |
| 6,377,848 B1 | 4/2002 | Garde et al. |
| 6,391,005 B1 | 5/2002 | Lum et al. |
| 6,423,029 B1 | 7/2002 | Elsberry |
| D465,026 S | 10/2002 | May et al. |
| 6,458,102 B1 | 10/2002 | Mann et al. |
| 6,485,461 B1 | 11/2002 | Mason et al. |
| 6,485,465 B2 | 11/2002 | Moberg et al. |
| 6,500,150 B1 | 12/2002 | Gross et al. |
| 6,503,231 B1 | 1/2003 | Prausnitz et al. |
| 6,511,336 B1 | 1/2003 | Turek et al. |
| 6,517,517 B1 | 2/2003 | Farrugia et al. |
| D471,274 S | 3/2003 | Diaz et al. |
| D471,983 S | 3/2003 | Hippolyte et al. |
| 6,558,351 B1 | 5/2003 | Steil et al. |
| 6,589,229 B1 | 7/2003 | Connelly et al. |
| 6,595,956 B1 | 7/2003 | Gross et al. |
| 6,595,960 B2 | 7/2003 | West et al. |
| 6,645,181 B1 | 11/2003 | Lavi et al. |
| 6,652,482 B2 | 11/2003 | Hochman |
| 6,656,158 B2 | 12/2003 | Mahoney et al. |
| 6,656,159 B2 | 12/2003 | Flaherty |
| 6,659,980 B2 | 12/2003 | Moberg et al. |
| 6,673,033 B1 | 1/2004 | Sciulli et al. |
| 6,679,862 B2 | 1/2004 | Diaz et al. |
| 6,689,118 B2 | 2/2004 | Alchas et al. |
| 6,699,218 B2 | 3/2004 | Flaherty et al. |
| 6,722,916 B2 | 4/2004 | Buccinna et al. |
| 6,743,211 B1 | 6/2004 | Prausnitz et al. |
| 6,749,587 B2 | 6/2004 | Flaherty |
| 6,752,787 B1 | 6/2004 | Causey, III et al. |
| 6,768,425 B2 | 7/2004 | Flaherty et al. |
| 6,786,890 B2 | 9/2004 | Preuthun et al. |
| 6,800,071 B1 | 10/2004 | McConnell et al. |
| 6,805,687 B2 | 10/2004 | Dextradeur et al. |
| 6,824,529 B2 | 11/2004 | Gross et al. |
| 6,843,782 B2 | 1/2005 | Gross et al. |
| 6,854,620 B2 | 2/2005 | Ramey |
| 6,905,298 B1 | 6/2005 | Haring |
| 6,908,452 B2 | 6/2005 | Diaz et al. |
| 6,960,192 B1 | 11/2005 | Flaherty et al. |
| 6,997,727 B1 | 2/2006 | Legrady et al. |
| 7,001,360 B2 | 2/2006 | Veasey et al. |
| 7,034,223 B2 | 4/2006 | Fan et al. |
| 7,048,715 B2 | 5/2006 | Diaz et al. |
| 7,060,054 B2 | 6/2006 | Nissels |
| 7,060,059 B2 | 6/2006 | Keith et al. |
| 7,097,637 B2 | 8/2006 | Triplett et al. |
| 7,128,727 B2 | 10/2006 | Flaherty et al. |
| 7,144,384 B2 | 12/2006 | Gorman et al. |
| D544,092 S | 6/2007 | Lewis |
| 7,225,694 B2 | 6/2007 | Said |
| 7,247,149 B2 | 7/2007 | Beyerlein |

(56) References Cited

U.S. PATENT DOCUMENTS

| | | |
|---|---|---|
| 7,250,037 B2 | 7/2007 | Shermer et al. |
| 7,267,669 B2 | 9/2007 | Staunton et al. |
| 7,291,132 B2 | 11/2007 | DeRuntz et al. |
| 7,291,159 B2 | 11/2007 | Schmelzeisen-Redeker et al. |
| 7,303,549 B2 | 12/2007 | Flaherty et al. |
| 7,344,385 B2 | 3/2008 | Chen |
| 7,364,570 B2 | 4/2008 | Gerondale et al. |
| 7,390,314 B2 | 6/2008 | Stutz, Jr. et al. |
| 7,407,493 B2 | 8/2008 | Cane' |
| D578,210 S | 10/2008 | Muta et al. |
| 7,455,663 B2 | 11/2008 | Bikovsky |
| 7,465,290 B2 | 12/2008 | Reilly |
| 7,488,181 B2 | 2/2009 | van Haaster |
| 7,497,842 B2 | 3/2009 | Diaz et al. |
| 7,501,587 B2 | 3/2009 | English |
| 7,503,786 B2 | 3/2009 | Kato et al. |
| 7,530,964 B2 | 5/2009 | Lavi et al. |
| 7,547,281 B2 | 6/2009 | Hayes et al. |
| 7,565,208 B2 | 7/2009 | Harris et al. |
| 7,569,050 B2 | 8/2009 | Moberg et al. |
| D600,341 S | 9/2009 | Loerwald |
| 7,585,287 B2 | 9/2009 | Bresina et al. |
| 7,588,559 B2 | 9/2009 | Aravena et al. |
| 7,589,974 B2 | 9/2009 | Grady et al. |
| D602,155 S | 10/2009 | Foley et al. |
| D602,586 S | 10/2009 | Foley et al. |
| D604,835 S | 11/2009 | Conley |
| 7,628,770 B2 | 12/2009 | Ethelfeld |
| 7,628,772 B2 | 12/2009 | McConnell et al. |
| 7,628,782 B2 | 12/2009 | Adair et al. |
| 7,637,891 B2 | 12/2009 | Wall |
| 7,637,899 B2 | 12/2009 | Woolston et al. |
| 7,641,649 B2 | 1/2010 | Moberg et al. |
| 7,660,627 B2 | 2/2010 | McNichols et al. |
| 7,678,079 B2 | 3/2010 | Shermer et al. |
| 7,682,338 B2 | 3/2010 | Griffin |
| 7,686,787 B2 | 3/2010 | Moberg et al. |
| 7,699,829 B2 | 4/2010 | Harris et al. |
| 7,699,833 B2 | 4/2010 | Moberg et al. |
| 7,704,088 B2 | 4/2010 | Sakamoto |
| 7,704,227 B2 | 4/2010 | Moberg et al. |
| 7,704,229 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,913 B2 | 5/2010 | Novak et al. |
| 7,722,574 B2 | 5/2010 | Toman et al. |
| 7,736,344 B2 | 6/2010 | Moberg et al. |
| 7,744,589 B2 | 6/2010 | Mounce et al. |
| 7,749,194 B2 | 7/2010 | Edwards et al. |
| 7,776,030 B2 | 8/2010 | Estes et al. |
| 7,780,637 B2 | 8/2010 | Jerde et al. |
| 7,789,857 B2 | 9/2010 | Moberg et al. |
| 7,801,599 B2 | 9/2010 | Young et al. |
| 7,806,868 B2 | 10/2010 | De Polo et al. |
| 7,828,528 B2 | 11/2010 | Estes et al. |
| 7,837,659 B2 | 11/2010 | Bush, Jr. et al. |
| 7,846,132 B2 | 12/2010 | Gravesen et al. |
| 7,854,723 B2 | 12/2010 | Hwang et al. |
| 7,857,131 B2 | 12/2010 | Vedrine |
| 7,879,025 B2 | 2/2011 | Jacobson et al. |
| 7,918,825 B2 | 4/2011 | O'Connor et al. |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,955,305 B2 | 6/2011 | Moberg et al. |
| 7,967,784 B2 | 6/2011 | Pongpairochana et al. |
| 7,967,795 B1 | 6/2011 | Cabiri |
| 7,981,105 B2 | 7/2011 | Adair et al. |
| 7,988,683 B2 | 8/2011 | Adair et al. |
| 7,993,300 B2 | 8/2011 | Nyholm et al. |
| 7,993,301 B2 | 8/2011 | Boyd et al. |
| 7,998,111 B2 | 8/2011 | Moberg et al. |
| 8,021,357 B2 | 9/2011 | Tanaka et al. |
| 8,025,658 B2 | 9/2011 | Chong et al. |
| 8,029,469 B2 | 10/2011 | Ethelfeld |
| 8,034,019 B2 | 10/2011 | Nair et al. |
| 8,038,666 B2 | 10/2011 | Triplett et al. |
| 8,057,431 B2 | 11/2011 | Woehr et al. |
| 8,057,436 B2 | 11/2011 | Causey et al. |
| 8,062,253 B2 | 11/2011 | Nielsen et al. |
| 8,066,694 B2 | 11/2011 | Wagener |
| D650,079 S | 12/2011 | Presta et al. |
| D650,903 S | 12/2011 | Kosinski et al. |
| 8,086,306 B2 | 12/2011 | Katzman et al. |
| D652,503 S | 1/2012 | Cameron et al. |
| 8,105,279 B2 | 1/2012 | Mernoe et al. |
| 8,114,046 B2 | 2/2012 | Covino et al. |
| 8,114,064 B2 | 2/2012 | Alferness et al. |
| 8,114,066 B2 | 2/2012 | Naef et al. |
| D657,462 S | 4/2012 | Siroky |
| 8,147,446 B2 | 4/2012 | Yodfat et al. |
| 8,152,764 B2 | 4/2012 | Istoc et al. |
| 8,152,770 B2 | 4/2012 | Reid |
| 8,152,779 B2 | 4/2012 | Cabiri |
| 8,152,793 B2 | 4/2012 | Keinanen et al. |
| 8,157,693 B2 | 4/2012 | Waksmundzki |
| 8,157,769 B2 | 4/2012 | Cabiri |
| 8,162,674 B2 | 4/2012 | Cho et al. |
| 8,162,923 B2 | 4/2012 | Adams et al. |
| 8,167,841 B2 | 5/2012 | Teisen-Simony et al. |
| 8,172,591 B2 | 5/2012 | Wertz |
| 8,172,804 B2 | 5/2012 | Bikovsky |
| 8,182,462 B2 | 5/2012 | Istoc et al. |
| 8,197,444 B1 | 6/2012 | Bazargan et al. |
| 8,206,351 B2 | 6/2012 | Sugimoto et al. |
| 8,221,356 B2 | 7/2012 | Enggaard et al. |
| 8,267,921 B2 | 9/2012 | Yodfat et al. |
| 8,287,520 B2 | 10/2012 | Drew et al. |
| 8,292,647 B1 | 10/2012 | McGrath et al. |
| 8,308,679 B2 | 11/2012 | Hanson et al. |
| 8,323,250 B2 | 12/2012 | Chong et al. |
| 8,372,039 B2 | 2/2013 | Mernoe et al. |
| 8,373,421 B2 | 2/2013 | Lindegger et al. |
| 8,409,142 B2 | 4/2013 | Causey et al. |
| 8,414,557 B2 | 4/2013 | Istoc et al. |
| 8,430,847 B2 | 4/2013 | Mernoe et al. |
| 8,465,455 B2 | 6/2013 | Cabiri |
| 8,469,942 B2 | 6/2013 | Kow et al. |
| 8,474,332 B2 | 7/2013 | Bente, IV et al. |
| 8,475,408 B2 | 7/2013 | Mernoe et al. |
| 8,479,595 B2 | 7/2013 | Vazquez et al. |
| 8,495,918 B2 | 7/2013 | Bazargan et al. |
| 8,496,862 B2 | 7/2013 | Zelkovich et al. |
| 8,512,287 B2 | 8/2013 | Cindrich et al. |
| 8,517,987 B2 | 8/2013 | Istoc et al. |
| 8,523,803 B1 | 9/2013 | Favreau |
| 8,556,856 B2 | 10/2013 | Bazargan et al. |
| 8,562,364 B2 | 10/2013 | Lin et al. |
| 8,574,216 B2 | 11/2013 | Istoc et al. |
| 8,603,026 B2 | 12/2013 | Favreau |
| 8,603,027 B2 | 12/2013 | Favreau |
| 8,628,510 B2 | 1/2014 | Bazargan et al. |
| 8,674,288 B2 | 3/2014 | Hanson et al. |
| 8,679,060 B2 | 3/2014 | Mernoe et al. |
| 8,690,855 B2 | 4/2014 | Alderete, Jr. et al. |
| 8,708,961 B2 | 4/2014 | Field et al. |
| 8,751,237 B2 | 6/2014 | Kubota |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian, Jr. et al. |
| 8,777,896 B2 | 7/2014 | Starkweather et al. |
| 8,777,924 B2 | 7/2014 | Kanderian, Jr. et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,790,295 B1 | 7/2014 | Sigg et al. |
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |

(56) References Cited

U.S. PATENT DOCUMENTS

| | | |
|---|---|---|
| 8,801,679 B2 | 8/2014 | Iio et al. |
| 8,810,394 B2 | 8/2014 | Kalpin |
| 8,814,379 B2 | 8/2014 | Griffiths et al. |
| 8,920,374 B2 | 12/2014 | Bokelman et al. |
| 9,061,104 B2 | 6/2015 | Daniel |
| 9,061,110 B2 | 6/2015 | Avery et al. |
| 9,089,475 B2 | 7/2015 | Fangrow |
| 9,089,641 B2 | 7/2015 | Kavazov |
| 2001/0025168 A1 | 9/2001 | Gross et al. |
| 2001/0041869 A1 | 11/2001 | Causey et al. |
| 2002/0010423 A1 | 1/2002 | Gross et al. |
| 2002/0029018 A1 | 3/2002 | Jeffrey |
| 2002/0040208 A1 | 4/2002 | Flaherty et al. |
| 2002/0055711 A1 | 5/2002 | Lavi et al. |
| 2002/0065488 A1 | 5/2002 | Suzuki et al. |
| 2002/0107487 A1 | 8/2002 | Preuthun |
| 2002/0123740 A1 | 9/2002 | Flaherty et al. |
| 2002/0161332 A1 | 10/2002 | Ramey |
| 2002/0169215 A1 | 11/2002 | Meng |
| 2003/0009133 A1 | 1/2003 | Ramey |
| 2003/0125671 A1 | 7/2003 | Aramata et al. |
| 2003/0135159 A1 | 7/2003 | Daily et al. |
| 2003/0160683 A1 | 8/2003 | Blomquist |
| 2003/0171717 A1 | 9/2003 | Farrugia et al. |
| 2003/0229308 A1 | 12/2003 | Tsals et al. |
| 2004/0010207 A1 | 1/2004 | Flaherty et al. |
| 2004/0092873 A1 | 5/2004 | Moberg |
| 2004/0116866 A1 | 6/2004 | Gorman et al. |
| 2004/0127857 A1 | 7/2004 | Shemesh et al. |
| 2004/0158172 A1 | 8/2004 | Hancock |
| 2004/0186419 A1 | 9/2004 | Cho |
| 2004/0260233 A1 | 12/2004 | Garibotto et al. |
| 2005/0033234 A1 | 2/2005 | Sadowski et al. |
| 2005/0065466 A1 | 3/2005 | Vedrine |
| 2005/0065472 A1 | 3/2005 | Cindrich et al. |
| 2005/0071487 A1 | 3/2005 | Lu et al. |
| 2005/0113761 A1 | 5/2005 | Faust et al. |
| 2005/0135078 A1* | 6/2005 | Hamada ............... G03B 15/05 362/3 |
| 2005/0159706 A1 | 7/2005 | Wilkinson et al. |
| 2005/0171476 A1 | 8/2005 | Judson et al. |
| 2005/0171512 A1 | 8/2005 | Flaherty |
| 2005/0177136 A1 | 8/2005 | Miller |
| 2005/0197650 A1 | 9/2005 | Sugimoto et al. |
| 2005/0203461 A1 | 9/2005 | Flaherty et al. |
| 2005/0238507 A1 | 10/2005 | Dilanni et al. |
| 2005/0283114 A1 | 12/2005 | Bresina et al. |
| 2006/0013716 A1 | 1/2006 | Nason et al. |
| 2006/0030816 A1 | 2/2006 | Zubry |
| 2006/0095014 A1 | 5/2006 | Ethelfeld |
| 2006/0122577 A1 | 6/2006 | Poulsen et al. |
| 2006/0173406 A1 | 8/2006 | Hayes et al. |
| 2006/0173439 A1 | 8/2006 | Thorne et al. |
| 2006/0195029 A1 | 8/2006 | Shults et al. |
| 2006/0211982 A1 | 9/2006 | Prestrelski et al. |
| 2006/0229569 A1 | 10/2006 | Lavi et al. |
| 2006/0264889 A1 | 11/2006 | Moberg et al. |
| 2006/0264890 A1 | 11/2006 | Moberg et al. |
| 2006/0264894 A1 | 11/2006 | Moberg et al. |
| 2006/0270987 A1 | 11/2006 | Peter |
| 2006/0283465 A1 | 12/2006 | Nickel et al. |
| 2006/0293722 A1 | 12/2006 | Slatkine et al. |
| 2007/0021733 A1 | 1/2007 | Hansen et al. |
| 2007/0049865 A1 | 3/2007 | Radmer et al. |
| 2007/0073228 A1 | 3/2007 | Mernoe et al. |
| 2007/0118405 A1 | 5/2007 | Campbell et al. |
| 2007/0167912 A1 | 7/2007 | Causey et al. |
| 2007/0185449 A1 | 8/2007 | Mernoe |
| 2007/0197968 A1 | 8/2007 | Pongpairochana et al. |
| 2007/0203454 A1 | 8/2007 | Shermer et al. |
| 2007/0233038 A1 | 10/2007 | Pruitt et al. |
| 2007/0282269 A1 | 12/2007 | Carter et al. |
| 2008/0021439 A1 | 1/2008 | Brittingham et al. |
| 2008/0033367 A1 | 2/2008 | Haury et al. |
| 2008/0033369 A1 | 2/2008 | Kohlbrenner et al. |
| 2008/0033393 A1 | 2/2008 | Edwards et al. |
| 2008/0051711 A1 | 2/2008 | Mounce et al. |
| 2008/0051730 A1 | 2/2008 | Bikovsky |
| 2008/0059133 A1 | 3/2008 | Edwards et al. |
| 2008/0097381 A1 | 4/2008 | Moberg et al. |
| 2008/0108951 A1 | 5/2008 | Jerde et al. |
| 2008/0140006 A1 | 6/2008 | Eskuri et al. |
| 2008/0140018 A1 | 6/2008 | Enggaard et al. |
| 2008/0147004 A1 | 6/2008 | Mann et al. |
| 2008/0167641 A1 | 7/2008 | Hansen et al. |
| 2008/0188813 A1 | 8/2008 | Miller et al. |
| 2008/0208138 A1 | 8/2008 | Lim et al. |
| 2008/0215006 A1 | 9/2008 | Thorkild |
| 2008/0215015 A1 | 9/2008 | Cindrich et al. |
| 2008/0243087 A1 | 10/2008 | Enggaard et al. |
| 2008/0249473 A1 | 10/2008 | Rutti et al. |
| 2008/0262436 A1 | 10/2008 | Olson |
| 2008/0269687 A1 | 10/2008 | Chong et al. |
| 2008/0269723 A1 | 10/2008 | Mastrototaro et al. |
| 2008/0274630 A1 | 11/2008 | Shelton et al. |
| 2008/0294143 A1 | 11/2008 | Tanaka et al. |
| 2008/0306449 A1 | 12/2008 | Kristensen et al. |
| 2008/0312601 A1 | 12/2008 | Cane |
| 2008/0319416 A1 | 12/2008 | Yodfat et al. |
| 2009/0041805 A1 | 2/2009 | Walker |
| 2009/0048347 A1 | 2/2009 | Cohen et al. |
| 2009/0054750 A1 | 2/2009 | Jennewine |
| 2009/0069784 A1 | 3/2009 | Estes et al. |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093792 A1 | 4/2009 | Gross et al. |
| 2009/0093793 A1 | 4/2009 | Gross et al. |
| 2009/0105650 A1 | 4/2009 | Wiegel et al. |
| 2009/0124977 A1 | 5/2009 | Jensen |
| 2009/0143730 A1 | 6/2009 | De Polo et al. |
| 2009/0143735 A1 | 6/2009 | De Polo et al. |
| 2009/0149830 A1 | 6/2009 | Spector |
| 2009/0182277 A1 | 7/2009 | Carter |
| 2009/0204076 A1 | 8/2009 | Liversidge |
| 2009/0209896 A1 | 8/2009 | Selevan |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259176 A1 | 10/2009 | Yairi |
| 2009/0281585 A1 | 11/2009 | Katzman et al. |
| 2009/0299290 A1 | 12/2009 | Moberg |
| 2009/0299397 A1 | 12/2009 | Ruan et al. |
| 2009/0326459 A1 | 12/2009 | Shipway et al. |
| 2009/0326509 A1 | 12/2009 | Muse et al. |
| 2010/0030156 A1 | 2/2010 | Beebe et al. |
| 2010/0030198 A1 | 2/2010 | Beebe et al. |
| 2010/0049128 A1 | 2/2010 | McKenzie et al. |
| 2010/0049144 A1 | 2/2010 | McConnell et al. |
| 2010/0057057 A1 | 3/2010 | Hayter et al. |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0137831 A1 | 6/2010 | Tsals |
| 2010/0145303 A1 | 6/2010 | Yodfat et al. |
| 2010/0145305 A1 | 6/2010 | Alon |
| 2010/0162548 A1 | 7/2010 | Leidig |
| 2010/0168607 A1 | 7/2010 | Miesel |
| 2010/0168683 A1 | 7/2010 | Cabiri |
| 2010/0198157 A1 | 8/2010 | Gyrn et al. |
| 2010/0204657 A1 | 8/2010 | Yodfat et al. |
| 2010/0234767 A1 | 9/2010 | Sarstedt |
| 2010/0234830 A1 | 9/2010 | Straessler et al. |
| 2010/0241065 A1 | 9/2010 | Moberg et al. |
| 2010/0264931 A1 | 10/2010 | Lindegger et al. |
| 2010/0274112 A1 | 10/2010 | Hoss et al. |
| 2010/0274192 A1 | 10/2010 | Mernoe |
| 2010/0280499 A1 | 11/2010 | Yodfat et al. |
| 2010/0331826 A1 | 12/2010 | Field et al. |
| 2011/0034900 A1 | 2/2011 | Yodfat et al. |

(56) References Cited

U.S. PATENT DOCUMENTS

| | | |
|---|---|---|
| 2011/0054399 A1 | 3/2011 | Chong et al. |
| 2011/0054400 A1 | 3/2011 | Chong et al. |
| 2011/0125056 A1 | 5/2011 | Merchant |
| 2011/0160654 A1 | 6/2011 | Hanson et al. |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0172745 A1 | 7/2011 | Na et al. |
| 2011/0178472 A1 | 7/2011 | Cabiri |
| 2011/0201998 A1 | 8/2011 | Pongpairochana et al. |
| 2011/0238031 A1 | 9/2011 | Adair et al. |
| 2011/0245773 A1 | 10/2011 | Estes et al. |
| 2011/0270160 A1 | 11/2011 | Mernoe |
| 2011/0282282 A1 | 11/2011 | Lorenzen et al. |
| 2011/0282296 A1 | 11/2011 | Harms et al. |
| 2011/0295205 A1 | 12/2011 | Kaufmann et al. |
| 2011/0313238 A1 | 12/2011 | Reichenbach et al. |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022344 A1 | 1/2012 | Kube |
| 2012/0022499 A1 | 1/2012 | Anderson et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041414 A1 | 2/2012 | Estes et al. |
| 2012/0071828 A1 | 3/2012 | Tojo et al. |
| 2012/0096953 A1 | 4/2012 | Bente, IV et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0129362 A1 | 5/2012 | Hampo et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0226234 A1 | 9/2012 | Bazargan et al. |
| 2012/0259282 A1 | 10/2012 | Alderete, Jr. et al. |
| 2013/0012875 A1 | 1/2013 | Gross et al. |
| 2013/0068319 A1 | 3/2013 | Plumptre et al. |
| 2013/0085457 A1 | 4/2013 | Schiff et al. |
| 2013/0089992 A1 | 4/2013 | Yang |
| 2013/0096509 A1 | 4/2013 | Avery et al. |
| 2013/0110049 A1 | 5/2013 | Cronenberg et al. |
| 2013/0133438 A1 | 5/2013 | Kow et al. |
| 2013/0237953 A1 | 9/2013 | Kow et al. |
| 2013/0245595 A1 | 9/2013 | Kow et al. |
| 2013/0245596 A1 | 9/2013 | Cabiri et al. |
| 2013/0253419 A1 | 9/2013 | Favreau |
| 2013/0253420 A1 | 9/2013 | Favreau |
| 2013/0253421 A1 | 9/2013 | Favreau |
| 2013/0296799 A1 | 11/2013 | Degtiar et al. |
| 2013/0304021 A1 | 11/2013 | Cabiri et al. |
| 2013/0323699 A1 | 12/2013 | Edwards et al. |
| 2013/0331791 A1 | 12/2013 | Gross et al. |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0128807 A1 | 5/2014 | Moberg et al. |
| 2014/0128835 A1 | 5/2014 | Moberg et al. |
| 2014/0135692 A1 | 5/2014 | Alderete, Jr. et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete, Jr. et al. |
| 2014/0194819 A1 | 7/2014 | Maule et al. |
| 2014/0194854 A1 | 7/2014 | Tsals |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0213975 A1 | 7/2014 | Clemente et al. |
| 2014/0228768 A1 | 8/2014 | Eggert et al. |
| 2014/0236087 A1 | 8/2014 | Alderete, Jr. et al. |
| 2014/0261758 A1 | 9/2014 | Wlodarczyk et al. |
| 2015/0045729 A1 | 2/2015 | Denzer et al. |

FOREIGN PATENT DOCUMENTS

| | | |
|---|---|---|
| CN | 101090749 A | 12/2007 |
| CN | 201941304 U | 8/2011 |
| CN | 102186733 A | 9/2011 |
| DE | 1064693 B | 9/1959 |
| EP | 0017412 A1 | 10/1980 |
| EP | 0222656 A1 | 5/1987 |
| EP | 0401179 A1 | 12/1990 |
| EP | 1530979 A1 | 5/2005 |
| EP | 1666080 A1 | 6/2006 |
| EP | 2060606 A1 | 5/2009 |
| EP | 2498589 A1 | 9/2012 |
| JP | H07-194701 A | 8/1995 |
| JP | H09-505758 A | 6/1997 |
| JP | 2001-512992 A | 8/2001 |
| JP | 2002-505601 A | 2/2002 |
| JP | 2002-507459 A | 3/2002 |
| JP | 2002-528676 A | 9/2002 |
| JP | 2003-501157 A | 1/2003 |
| JP | 2003-527138 A | 9/2003 |
| JP | 2003-534061 A | 11/2003 |
| JP | 2004-501721 A | 1/2004 |
| JP | 2004-512100 A | 4/2004 |
| JP | 2005-523127 A | 8/2005 |
| JP | 2005-270629 A | 10/2005 |
| JP | 2007-509661 A | 4/2007 |
| JP | 2008-534131 A | 8/2008 |
| JP | 2008-220961 A | 9/2008 |
| JP | 2009-502273 A | 1/2009 |
| WO | 9009202 A1 | 8/1990 |
| WO | 9307922 A1 | 4/1993 |
| WO | 9407553 A1 | 4/1994 |
| WO | 9513838 A1 | 5/1995 |
| WO | 9609083 A1 | 3/1996 |
| WO | 9632975 A1 | 10/1996 |
| WO | 9700091 A1 | 1/1997 |
| WO | 9710012 A1 | 3/1997 |
| WO | 9733638 A1 | 9/1997 |
| WO | 9857683 A1 | 12/1998 |
| WO | 9929151 A1 | 6/1999 |
| WO | 9959665 A1 | 11/1999 |
| WO | 0025844 A1 | 5/2000 |
| WO | 0187384 A1 | 11/2001 |
| WO | 0189607 A2 | 11/2001 |
| WO | 0189613 A1 | 11/2001 |
| WO | 0202165 A2 | 1/2002 |
| WO | 0234315 A1 | 5/2002 |
| WO | 0272182 A1 | 9/2002 |
| WO | 03090833 A1 | 11/2003 |
| WO | 2004032990 A2 | 4/2004 |
| WO | 2004105841 A1 | 12/2004 |
| WO | 2005018703 A2 | 3/2005 |
| WO | 2005037350 A2 | 4/2005 |
| WO | 2006037434 A1 | 4/2006 |
| WO | 06069380 A1 | 6/2006 |
| WO | 2006102676 A1 | 9/2006 |
| WO | 2006104806 A2 | 10/2006 |
| WO | 2007051563 A1 | 5/2007 |
| WO | 2007056504 A1 | 5/2007 |
| WO | 2008001377 A2 | 1/2008 |
| WO | 2008014908 A1 | 2/2008 |
| WO | 2008057976 A2 | 5/2008 |
| WO | 2008072229 A2 | 6/2008 |
| WO | 2008076459 A1 | 6/2008 |
| WO | 2008078318 A2 | 7/2008 |
| WO | 2009044401 | 4/2009 |
| WO | 2009046989 A2 | 4/2009 |
| WO | 2009125398 A2 | 10/2009 |
| WO | 2009144085 A2 | 12/2009 |
| WO | 2010078227 A1 | 7/2010 |
| WO | 2010078242 A1 | 7/2010 |
| WO | 2011075105 A1 | 6/2011 |
| WO | 2011090955 A1 | 7/2011 |
| WO | 2011090956 A2 | 7/2011 |

(56) References Cited

FOREIGN PATENT DOCUMENTS

| WO | 2011156373 A1 | 12/2011 |
| WO | 2012032411 A2 | 3/2012 |
| WO | 2012040528 A1 | 3/2012 |
| WO | 2012160157 A1 | 11/2012 |
| WO | 2014179774 A1 | 11/2014 |

OTHER PUBLICATIONS

Office Action dated Feb. 24, 2015 in U.S. Appl. No. 14/258,661 by Cabiri.
U.S. Appl. No. 14/638,525 by Filman, filed Mar. 4, 2015.
Extended European Search Report dated Feb. 23, 2015 in EP Application No. 14166596.8.
Office Action dated Mar. 10, 2015 in U.S. Appl. No. 13/643,470 by Alon.
Office Action dated Mar. 10, 2015 in U.S. Appl. No. 12/244,666 by Gross.
Extended European Search Report dated Feb. 23, 2015 in EP Application No. 14166591.9.
Office Action dated Mar. 10, 2015 in CN Application No. 201180006567.4.
Office Action dated Mar. 31, 2015 in JP Application No. 2012-550068.
Int'l Preliminary Report on Patentability dated May 14, 2015 in Int'l Application No. PCT/US2013/065211.
Office Action dated May 7, 2015 in JP Application No. 2012-550069.
Office Action dated May 13, 2015 in CN Application No. 201380025566.3.
U.S. Appl. No. 14/715,791 by Cabiri, filed May 19, 2015.
U.S. Appl. No. 14/725,009 by Bar-El, filed May 29, 2015.
Office Action dated May 1, 2015 in U.S. Appl. No. 14/638,525 by Filman.
Office Action dated Jun. 4, 2015 in U.S. Appl. No. 13/667,739 by Cabiri.
Office Action dated Jul. 31, 2015 in U.S. Appl. No. 13/521,181 by Cabiri.
Office Action dated Aug. 13, 2015 in U.S. Appl. No. 14/553,399 by Cabiri.
Int'l Preliminary Report on Patentability dated Jul. 16, 2015 in Int'l Application No. PCT/US2013/078040.
Notice of Allowance dated Aug. 24, 2015 in U.S. Appl. No. 29/479,307 by Norton.
Office Action dated Sep. 9, 2015 in U.S. Appl. No. 13/643,470 by Alon.
U.S. Appl. No. 14/850,450 by Gross, filed Sep. 10, 2015.
U.S. Appl. No. 14/861,478 by Cabiri, filed Sep. 22, 2015.
U.S. Appl. No. 14/880,673 by Cabiri, filed Oct. 12, 2015.
Office Action dated Sep. 30, 2015 in U.S. Appl. No. 13/667,739 by Cabiri.
Office Action dated Sep. 18, 2015 in U.S. Appl. No. 13/874,085 by Cabiri.
Extended European Search Report dated Jan. 20, 2017 in EP Application No. 16164319.2.
U.S. Appl. No. 29/479,307 by Norton, filed Jan. 14, 2014.
U.S. Appl. No. 14/193,692 by Gross, filed Feb. 28, 2014.
Office Action dated Feb. 4, 2014 in EP Application No. 11 707 942.6.
English translation of an Office Action dated Mar. 5, 2014 in CN Application No. 200880117084.X.
Int'l Search Report and Written Opinion dated Apr. 3, 2014 in Int'l Application No. PCT/US2013/078040.
Extended European Search Report dated Mar. 27, 2014 in EP Application No. 14154717.4.
Office Action dated Feb. 28, 2014 in CN Application No. 201180006571.0.
U.S. Appl. No. 14/258,661 by Cabiri, filed Apr. 22, 2014.
Int'l Search Report and Written Opinion dated Jan. 7, 2014 in Int'l Application No. PCT/US2013/065211.
Office Action dated May 23, 2014 in U.S. Appl. No. 13/472,112 by Cabiri.
Office Action dated Jun. 3, 2014 in JP Application No. 2010-527595.
Office Action dated Jul. 7, 2014 in U.S. Appl. No. 12/244,666 by Gross.
Int'l Search Report and Written Opinion dated Jul. 31, 2014 in Int'l Application No. PCT/US2014/033598.
Extended European Search Report dated Aug. 7, 2014 in EP Application No. 1417477.4.
Office Action dated Aug. 6, 2014 in EP Application No. 11 707 942.6.
Office Action dated Sep. 2, 2014 in JP Application No. 2012-550069.
Office Action dated Sep. 2, 2014 in JP Application No. 2012-550068.
Office Action dated Aug. 26, 2014 in CN Application No. 201180006567.4.
Int'l Preliminary Report on Patentability dated Oct. 9, 2014 in Int'l Application No. PCT/US2013/033118.
Office Action dated Oct. 9, 2014 in U.S. Appl. No. 13/873,335.
Office Action dated Nov. 5, 2014 in U.S. Appl. No. 13/643,470 by Alon.
U.S. Appl. No. 14/553,399 by Cabiri, filed Nov. 25, 2014.
Office Action dated Nov. 2, 2014 in CN Application No. 201180006571.0.
Office Action dated Nov. 21, 2014 in U.S. Appl. No. 13/472,112 by Cabiri.
Office Action dated Nov. 21, 2014 in U.S. Appl. No. 13/429,840 by Cabiri.
Int'l Preliminary Report on Patentability dated Nov. 27, 2014 in Int'l Application No. PCT/US2013/039465.
U.S. Appl. No. 14/593,051 by Gross, filed Jan. 9, 2015.
Int'l Search Report dated May 13, 2009 in Int'l Application No. PCT/IL2008/001312.
Int'l Preliminary Report on Patentability dated Apr. 7, 2010 in Int'l Application No. PCT/IL2008/001312; Written Opinion.
Int'l Search Report dated Apr. 26, 2010 in Int'l Application No. PCT/US2009/069552.
Office Action dated Apr. 5, 2010 in U.S. Appl. No. 12/244,666.
Office Action dated Sep. 21, 2010 in U.S. Appl. No. 12/244,666.
Office Action dated Apr. 5, 2010 in U.S. Appl. No. 12/244,688.
Office Action dated Sep. 2, 2010 in U.S. Appl. No. 12/244,688.
Office Action dated Sep. 30, 2010 in U.S. Appl. No. 12/689,250.
Int'l Search Report dated Jan. 12, 2011 in Int'l Application No. PCT/US2010/048556; Written Opinion.
International Preliminary Report on Patentability dated Jul. 5, 2011 in International Application No. PCT/US2009/069552; Written Opinion.
Office Action dated Jul. 13, 2011 in U.S. Appl. No. 12/559,563.
Int'l Preliminary Report on Patentability dated Sep. 1, 2011 in Int'l Application No. PCT/US2010/048556.
Office Action dated Sep. 6, 2011 in U.S. Appl. No. 12/345,818.
Office Action dated Feb. 21, 2012 in U.S. Appl. No. 12/689,249.
Int'l Search Report dated Jun. 17, 2011 in Int'l Application No. PCT/US2011/021604.
Int'l Search Report dated Oct. 12, 2011 in Int'l Application No. PCT/US2011/021605.
Office Action dated Oct. 28, 2011 in U.S. Appl. No. 12/615,828.
Int'l Search Report dated Sep. 22, 2011 in Int'l Application No. PCT/IL11/00368; Written Opinion.
U.S. Appl. No. 13/521,181 by Cabiri, filed Jul. 9, 2012.
U.S. Appl. No. 13/521,167 by Cabiri, filed Jul. 9, 2012.
Office Action dated May 16, 2012 in U.S. Appl. No. 12/615,828.
Office Action dated Jul. 2, 2012 in U.S. Appl. No. 13/272,555.
Office Action dated May 3, 2012 in CN Application No. 200880117084.X.
U.S. Appl. No. 13/472,112 by Cabiri, filed May 15, 2012.
U.S. Appl. No. 13/429,840 by Cabiri, filed Mar. 26, 2012.
Int'l Preliminary Report on Patentability dated Aug. 2, 2012 in Int'l Application No. PCT/US2011/021604.
U.S. Appl. No. 13/643,470 by Alon, filed Oct. 25, 2012.
U.S. Appl. No. 13/733,516 by Cabiri, filed Jan. 3, 2013.

(56) References Cited

OTHER PUBLICATIONS

Office Action dated Jan. 8, 2013 in JP Application No. 2010-527595.
Int'l Preliminary Report on Patentability dated Feb. 7, 2013 in Int'l Application No. PCT/US2011/021604.
Int'l Preliminary Report on Patentability dated Feb. 7, 2013 in Int'l Application No. PCT/US2011/021605.
English translation of an Office Action dated Jan. 30, 2013 in CN Application No. 200880117084.X.
U.S. Appl. No. 13/873,335 by Filman, filed Apr. 30, 2013.
U.S. Appl. No. 13/892,905 by Cabiri, filed May 13, 2013.
U.S. Appl. No. 13/874,121 by Degtiar, filed Apr. 30, 2013.
U.S. Appl. No. 13/874,085 by Cabiri, filed Apr. 30, 2013.
U.S. Appl. No. 13/874,017 by Cabiri, filed Apr. 30, 2013.
Int'l Search Report and Written Opinion dated Jul. 26, 2013 in Int'l Application No. PCT/US2012/039465.
Int'l Search Report and Written Opinion dated Aug. 5, 2013 in Int'l Application No. PCT/US2013/033118.
U.S. Appl. No. 13/964,651 by Gross, filed Aug. 12, 2013.
Office Action dated Aug. 15, 2013 in CN Application No. 200880117084.X.
Office Action dated Oct. 9, 2013 in IL Application No. 208634.
Office Action dated Nov. 5, 2013 in JP Application No. 2010-527595.
Office Action dated Sep. 29, 2013 in CN Application No. 201080040968.7.
Office Action dated Nov. 4, 2013 in EP Application No. 11 709 234.6.
Office Action dated Dec. 17, 2013 in JP Application No. 2012-529808.
Office Action dated Dec. 10, 2013 in CN Application No. 201180006567.4.
Office Action dated Jan. 8, 2014 in U.S. Appl. No. 13/521,167 by Cabiri.

\* cited by examiner

Figure 2

| Stage device | Payload status | Operator indicator | Action of operator |
|---|---|---|---|
| Off ~224 | Full – good/bad ~225a | None ~208e | Activate ~102 |
| Activated ~124a | Full – good/bad ~225a | Ready ~208a | Engage ~110 |
| Engaged ~124b | Partially full ~225b | Working ~208b | Wait ~209 |
| Disengaged ~124c | Empty / deployed ~225c | Safe to remove ~208c | Remove ~122 |
| Error ~124d | How much discharged ~225d | Error or none ~208d | Remove and contact supervisor |

223

REDUNDANT INJECTION DEVICE STATUS INDICATION

BACKGROUND OF THE INVENTION

The present invention, in some embodiments thereof, relates to an operator interface for a drug delivery device, more particularly, but not exclusively, to dual interface for giving potentially complex information and/or simple instructions relating to the state of an autoinjector.

U.S. Patent Application Publication no. 2014/0228768 to Eggert discloses "a handheld medical device having a housing, at least one operator activatable button mounted on a surface of the housing, and a light source mounted within the housing below the button and arranged to direct light towards the button. Substantially the whole of the button and the surface of the housing adjacent the button are opaque, save for a narrow strip adjacent the periphery of the button which is non-opaque."

U.S. Patent Application Publication no. 2014/0207080 to Allerdings "relates to a method and to a monitoring device for monitoring operation of a drug delivery device, the monitoring device comprising of at least a first and a second sensor arranged at a distance from each other with regard to a first direction and being adapted to generate a first and a second electrical signal in response to an operation of the device, a processing unit configured to determine a time delay between the first and the second electrical signals and being adapted to determine at least one state parameter of the drug delivery device on the basis of said time delay."

U.S. Patent Application Publication no. 2014/0171881 to the present inventor discloses, "a method of preparing a compound device for use. The device may include a sealed component and an active outer surface. The outer surface may be protected by a surface cover. Preparing the device may include activating the active outer surface by removing the surface cover and exposing an internal portion of the sealed component to the exterior of the device by unsealing the sealed component and synchronizing the activating and said unsealing using a coupler attached to the surface cover and the sealed component."

U.S. Patent Application Publication no. 2014/0163526 to the present inventor discloses that, "an automated injection device may be loaded with a standard type syringe and/or hypodermic needle. Optionally the syringe may be supplied loaded with medicine and/or covered with a sterile needle cover. The syringe may be loaded into the injector with in a sterile state with needle cover in place. Injector may include for example a fastener (for example an adhesive base). In some embodiments, the fastener may assist an operator to hold injector steady on the skin of a patient for an extended period. For example, injector may be used to give injections of volume ranging between 0.5 and 3.0 ml over a time period ranging between 30 sec to 180 sec."

Additional background art includes International Patent Application Publication no. WO2013173092 to the present inventor.

SUMMARY OF THE INVENTION

According to an aspect of some embodiments of the invention, there is provided a device for delivering a drug from a reservoir comprising: a housing with a space shaped to hold the reservoir; the housing defining an optical path from outside the device to an interior of the reservoir such that a payload status of the reservoir can be discerned from a vantage point outside the device; a generator of a coded light signal, the generator positioned so that at least a portion of the coded light signal travels along the optical path and is viewable from the vantage point.

According to some embodiments of the invention, the optical path includes a window within the housing.

According to some embodiments of the invention, the device further comprises: a sensor directed toward the space for sensing a status of the reservoir and wherein the generator is responsive to output of the sensor.

According to some embodiments of the invention, the device further comprises: a processor receiving a feedback from the device and the processor controlling the generator in accordance to the feedback.

According to some embodiments of the invention, the processor is configured to generate the code for a light signal to indicate that the apparatus is functioning properly.

According to some embodiments of the invention, the device further comprises: a sensor located within the housing directed toward the space for sensing a status of the reservoir and feedback includes an output of the sensor.

According to some embodiments of the invention, the sensor includes a position sensor sensing a position of the reservoir.

According to some embodiments of the invention, the device further comprises: a position sensor sensing a position of the reservoir and wherein the generator is responsive to output of the sensor.

According to some embodiments of the invention, the portion of an interior of the reservoir and the coded light signal are visible along the optical path simultaneously.

According to some embodiments of the invention, the generator is configured to generate the coded light signal to indicate that the apparatus is functioning properly.

According to some embodiments of the invention, the device further comprises: a position sensor operationally connected to the processor the sensor sensitive to a position of the reservoir and the feedback includes an output of the position sensor.

According to some embodiments of the invention, the generator is configured for illuminating at least a portion of the reservoir with the coded light.

According to some embodiments of the invention, the generator is configured for illuminating at least a portion of the reservoir with the coded light.

According to some embodiments of the invention, the generator is configured for obscuring at least a portion of the reservoir with the coded light.

According to some embodiments of the invention, the device further comprises the reservoir at least partially filled with the drug.

According to some embodiments of the invention, the generator generates the coded light signal in between 3 and 6 modes.

According to some embodiments of the invention, the device where the generator generates the coded light signal with three colors, a constant signal and a blinking signal.

According to an aspect of some embodiments of the invention, there is provided a device for delivering a drug from a reservoir comprising: A drug reservoir including a transparent portion through which an interior of the reservoir is visible such that a payload status of the reservoir can be discerned from a vantage point outside the device; a generator of a coded light signal, the generator positioned so that at least a portion of the coded light signal overlaps the transparent portion from the vantage point.

According to an aspect of some embodiments of the invention, there is provided a method of indicating a status of a system for delivering a drug the system including a housing and a reservoir for the drug, the method comprising: Exposing an internal portion of the reservoir a vantage point outside the housing via an optical path; generating a coded light signal; indicating a status of the device with the coded light signal transmitting the coded light signal along the optical path to the vantage point.

According to some embodiments of the invention, the method further includes: discharging the drug from the internal portion of the reservoir during delivery of the drug.

According to some embodiments of the invention, the method further comprises: illuminating the internal portion of the reservoir with the coded light signal.

According to some embodiments of the invention, the method further comprises: reflecting a portion of the coded light signal from the reservoir.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 2 is a state diagram illustrating states and/or stages of operation of a drug delivery device in accordance with an embodiment of the current invention;

DESCRIPTION OF SPECIFIC EMBODIMENTS OF THE INVENTION

Overview

Figure 1A:
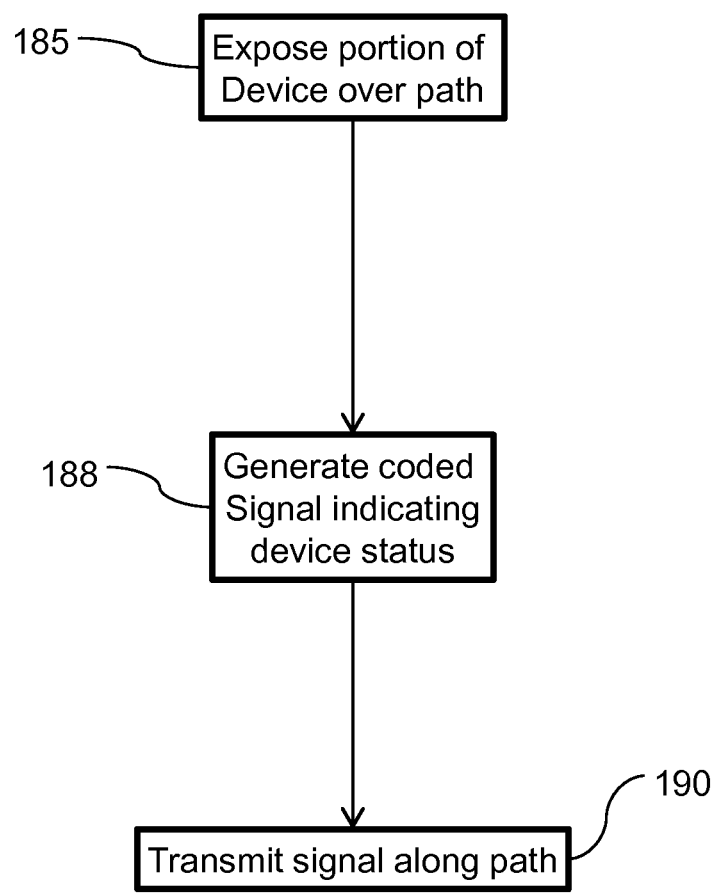
FIGS. 1A-1B are flow chart illustrations of indicating stages of operations and/or operator instructions of a drug delivery device in accordance with embodiments of the current invention.

The present invention, in some embodiments thereof, relates to an operator interface for a drug delivery device, more particularly, but not exclusively, to dual interface for giving potentially complex information and/or simple instructions relating to the state of an autoinjector.

An aspect of some embodiments of the present invention relates to a redundant status indicator for a drug delivery device. In some embodiments, the device includes an operator indicator. Optionally, the operator indicator is configured for simple interpretation. Alternatively or additionally, the operator indicator may be configured to clearly indicated and/or differentiate between stages and/or states that require actions. In some embodiments, the device may include a second indicator from which the status and/or stage of the device can be discerned. Optionally the operator indicator is configured to preferentially draw the attention of an operator of the device from the second indicator. For example the operator indicator and the second indicator may be viewed along a common optical path. For example the operator indicator and the second indicator may overlap.

In some embodiments, the operator indicator may be configured to avoid giving extra information that is not pertinent to simple operation of the device. For example the operator indicator may convey a coded indication. Optionally the coded indicator may have a small number of different modes. For example a coded indicator may have four modes or less modes. For example an operator indicator may have a ready, working, successfully finished, and error mode. Optionally the modes may be color coded. For example the ready mode may be blue. For example, the working mode and/or successfully finished mode may be green. For example, the error mode may be red. In some embodiments the operator indicator may have 3 to 6 modes. For example, three color coding may be combined with blinking vs. constant illumination. For example, the working mode may be blinking green while the successfully finished mode may be constant green. Optionally, there is a mode that indicates that the device can be engaged to a subject. Optionally there is a mode that indicates that the device may be removed from the subject. In some embodiments the operator indicator may have between 6 to 12 modes.

In some embodiments, the operator indicator and/or the second indicator may overlap. For example, from a viewpoint of an operator, when looking at the second indicator, the operator indicator may be visible within the area of the second indicator. For example, the operator indicator may reflect off of and/or be visible through and/or illuminate and/or over shadow the second indicator.

In some embodiments, the second indicator may give details that the operator indicator does not include, for example details that may at times not be pertinent to simple operation of the device. Alternatively or additionally, the second indicator may give status information under conditions where the operator indicator fails. For example the operator indicator may be an active indicator. The active indicator may in fails in some embodiments when the device (for example a battery) fails. The second indicator may optionally be a physical indicator which indicates a status even when the device fails.

For the sake of the current disclosure, an operator may be a person or multiple persons who operate a drug delivery device while it is in use and/or delivering the drug. A subject may include an individual who receives the drug. Optionally the subject may also be the operator.

In some embodiments the operator indicator may be configured to give necessary information to the operator when the device is working properly. When the device is not working properly, the operator indicator may optionally indicate a fault without giving detailed information. For example, for some errors, the operator indicator may just switch off. In some embodiments, switching off the indicator may indicate that something is wrong without indicating what the problem is. When a fault occurs an inexperienced operator may simply abort the delivery and/or contact a supervisor to get further instructions.

An aspect of some embodiments of the present invention relates to an operator indicator for a drug delivery device that attracts the operator's attention. For example, a drug delivery device may include a simple operator indicator and/or a complex status indicator. Optionally, the operator indicator is configured to attract the attention of an operator. For example, the operator indicator may include a light emitting diode (LED). Optionally, the second, complex status indicator may include a window for viewing a drug reservoir. For example, the attractive operator indicator may reduce the likelihood that the operator will misinterpret and/or be confused by the more complex second indicator. For example, the coded operator indicator may obscure, illuminate, appear within the space of, appear beside and/or surround the complex second indicator.

In some embodiments a housing of a drug delivery device may define an optical path (for example a window) through which the second indicator (for example a drug reservoir) may be viewed. Viewing the drug reservoir through the window may be a reliable indicator of the detailed status of various aspects of the medicine and/or delivery. In some cases an operator may become confused when trying to determine the status of the device from the reservoir (for example he may think that a slow moving plunger has stopped). Optionally, the device may also include a coded status indicator. For example, a LED may give off a coded signal (for example a color coded signal) indicating when the device is operating properly and/or when there is a fault in operation. For example, the coded signal may be visible in the same window as the reservoir. Optionally, the coded signal may be reflected off and/or refracted through the reservoir. Optionally the coded signal may illuminate the reservoir. For example the illumination may make it easier to see the status of the reservoir. Alternatively or additionally, the reflection and/or glare of the coded indicator may obscure the reservoir.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Methods of Displaying a Status of a Multi-Stage Drug Delivery Device

Referring now to the drawings, FIG. 1A is a flow chart illustration of a redundant method of indicating a status of a multi-stage drug delivery device in accordance with an embodiment of the current invention. In some embodiments, an optical path is supplied exposing 185 a portion of the device to an operator. Optionally, the exposed portion of the device may serve as a physical indicator of the status of the device. For example, an internal portion of a drug reservoir may be exposed 185. From internal portion of the reservoir it may be possible to discern the status of the payload of the reservoir and/or the status of the device. In some embodiments, a coded signal is generated 188 indicating a status of the device. Optionally the coded signal is transmitted 190 to the operator along optical path.

In some embodiments, the coded signal may indicate a status that relates directly to a user action. Optionally the exposed portion gives a more general concept of the state of the device. Optionally the coded status indicator will give an easily interpreted and/or easily discerned status indicator. Optionally, when activated, the coded indicator will be seen when the operator looks into the exposed portion of the device. For example, when the coded indicator is available, the user may be encouraged to use coded indicator and/or to pay less attention to the physical indicator.

Figure 1B:
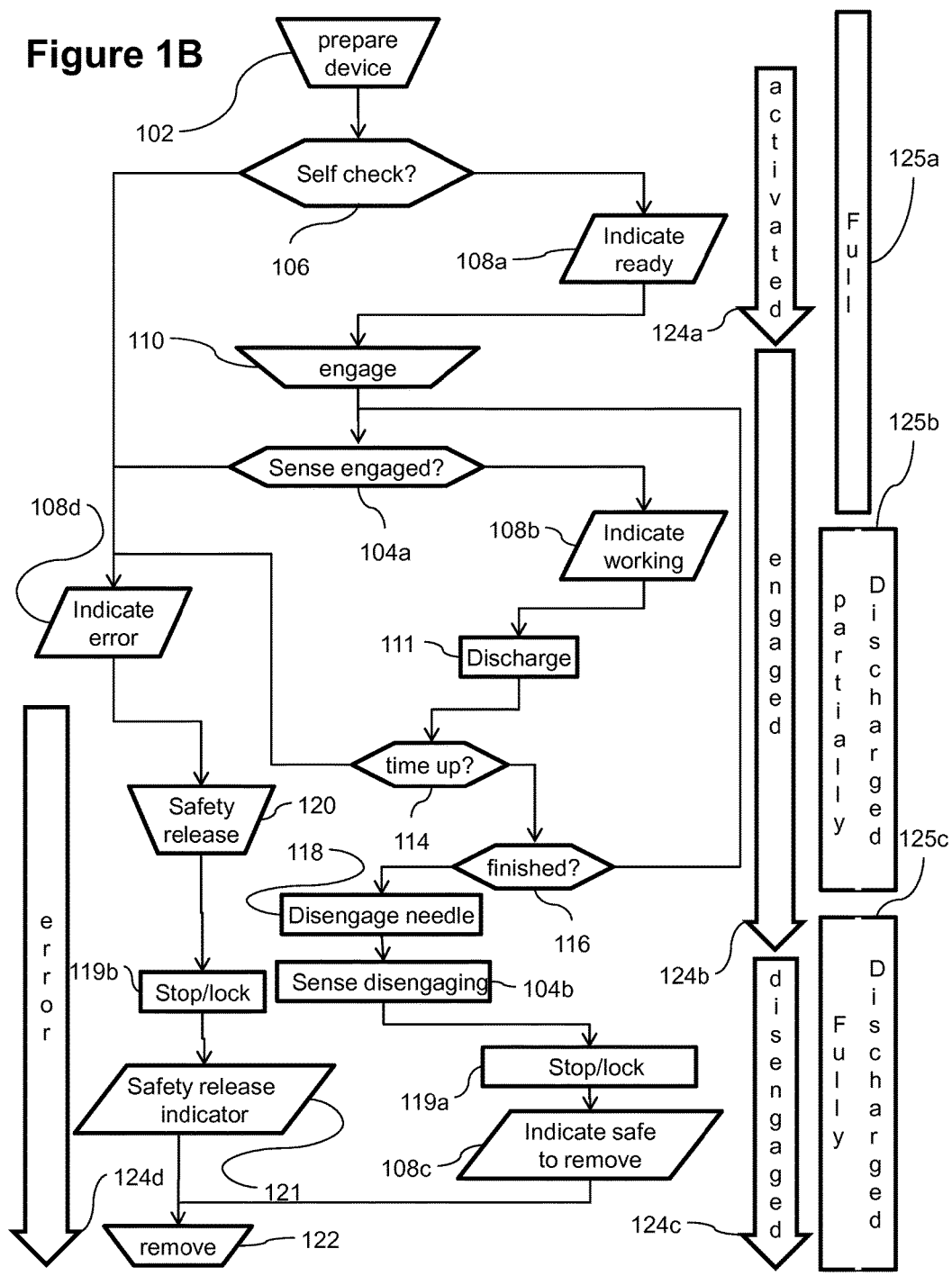

Referring now to the drawings, FIG. 1B is a flow chart illustration of a redundant method of indicating a status of a multi-stage drug delivery device in accordance with an embodiment of the current invention. Optionally, a drug delivery device may include an operator indicator and/or a second indicator. The operator indicator may be configured to communicate information that is pertinent to operator actions. For example, the operator interface may indicate when the device is working properly and/or not expected an operator intervention, when the device is awaiting an operator intervention (for example engaging and/or removing the device), when there is an operational fault and/or when a user may want to make a elective intervention. The second indicator may have additional functionalities lacking in the operator interface. For example, the second indicator may be configured to give information that may not be pertinent to standard operation of the device and/or the second indicator may be configured to continue to give information when the device is not in operation. Optionally, the operator indicator may be configured to attract attention of the operator during operation of the device. For example, the operator indicator may be configured to attract attention of the operator away from the second indicator.

In some embodiments, a user may prepare 102 a device. For example, preparing 102 the device may include unpacking the device and/or a manual action following the like removing safety locker and/or needle protector and/or an adhesive cover and/or removing the device from a box. Optionally, preparing 102 the device will activate 124a the device. Optionally, preparing 102 an element that is external and/or that obviously impedes use may activate 124a an element that is internal and/or whose functioning is not obvious to the user. For example, preparing 102 the device may include removing a protective cover (for example a needle cover and/or an adhesive protector). The device may sense removal of the cover.

In some embodiments, upon activation 124a an output device (an operator indicator including for example an LED) may indicate 108a a ready status of the device. Alternatively or additionally, the device may run a self check 106. When the self check is successful, the operator indicator may indicate 108a the ready status. Optionally, the output device may include an LED. For example, the LED may glow blue, indicating that the device has been activated and/or is ready to be engaged 110.

In some embodiments, a second indicator may output aspects of the status of the device. For example, a drug distribution device may include an optical path through which to view a drug reservoir of the device. For the sake of the current disclosure, an optical path may be defined as a way in which light may travel and/or be transmitted between two locations. In some embodiments, the optical path may include no optical elements. For example, an optical path may be a window (optionally a window may include a transparent and/or translucent pane; alternatively or additionally a window may not include a pane). Looking through the window one optionally discerns the status of the device, the drug reservoir of the device, and/or the payload, for example including seeing a fluid volume and clearness of the fluid. For example, in activated state 124a, one may see that the drug reservoir is full 125a. Alternatively or additionally there may be an alternative indicator, for example an audio and/or a tactile indicator such as a noise and/or a vibration.

In some cases, a device may fail to activate properly (for example if the battery is faulty). In some embodiments, an operator can recognize a fault in activation because activation indication 108a did not appear. Alternatively or additionally, in some cases of an activation fault (for example if the device fails a self test) an error indication 108d may be conveyed to the operator (for example by the operator indicator). Upon recognizing a fault, the operator may optionally release 120 a safety shield and/or a manual override. Alternatively or additionally, for a fault occurring previous to engaging of the device to the subject, the operator may simply not engage the device. A faulty device may be returned to a supervisor and/or an operator may get instructions for continuation of treatment. For example, the supervisor may look into the window and see that the reservoir is full 125a and/or partially empty 125b. Optionally the second indicator conveys how much medicine remains to be discharged. In some embodiments, the operator interface may give coded data and/or information based on a decision analysis and/or binary information (for example should the user engage the injector [yes/no], has injection completed successfully [yes/no] and/or is there error [yes/no]. Optionally the second interface gives complex and/or quantitative information and/or raw data [for example how much of the drug remains]. In some embodiments the reservoir may include more than a single fluid or powder. Optionally distributing the drug includes mixing the materials. In some embodiments the state of the reservoir, for example full, partially full, empty, including separate materials, partially mixed materials and/or fully mixed materials may be visible to the user (for example through a window in the housing of the device). In some embodiments the user may be able to discern in the second indicator aspects of the quality of the drug for example its color and/or clarity.

In some embodiments, an operator may engage 110 a device after the device has been activated 124a. Optionally, when the device senses that it has been engaged 104a a working indication 108b may be conveyed to the operator (for example by the operator indicator) and/or the device may begin to discharge 111 a drug.

In some embodiments while the device is engaged 124b and/or discharging 111 the operator waits. Optionally, the operator indicator may convey to the operator a working properly indication 108b. The working properly indication 108b may give substantially immediate feedback and/or reassure the operator. For example during discharge an operator indicator may include a green light. For example, during discharging, the second indicator may indicate a partially full 125b contents of the reservoir that is slowly decreasing over time. A second indicator may optionally include a sound, for example a motor noise. An operator looking at the second indicator may not immediately understand if the contents are decreasing and/or the device is working properly.

In some embodiments, sensing the engaging 104a may include sensing movement of the needle and/or movement of an associated part of the device (for example a drug reservoir connected to the needle). In some embodiments engaging 110 the device may include moving of a needle tip that was behind a skin contacting element to protrude beyond the skin contacting element. Optionally, inserting a needle may include moving the needle and/or the reservoir with respect to a housing; alternatively or additionally, the housing may collapse (for instance be shortened) such that skin contact surface moves with respect to the needle and/or with respect to another part of the housing exposing the needle.

In some embodiments, when the device senses 104a that it has been engaged 110 to the subject, the device may enter a discharging stage 124b. For example, during discharging stage 124b the drug may be discharged 111 to the subject. Optionally, through the activated stage 124a the drug reservoir may remain in its originally filled state. During the discharge stage 124b, the reservoir optionally goes from is originally filled stage through a partially filled state to a final drained state. In some embodiments the reservoir may be visible to the operator to see the state of the drug and/or the fill state of the reservoir (initially filled, partially drained and/or fully drained). In some embodiments, the initially filled reservoir may be filled to capacity. Alternatively or additionally, in the initially filled state, the reservoir may only be partially filled, for example between 90 to 100% and/or between 50 to 90% and/or between 20 to 50% capacity.

In some embodiments, when the discharge finishes 116 the device may disengage 118 from the subject. For example, the device may disengage 118 when the reservoir reaches a fully drained state. In the fully drained state the reservoir may be substantially empty. For example disengagement 118 may include retracting the needle and/or reservoir and/or plunger. In some embodiments, discharge 111 may end before the reservoir is empty. For example discharge may end when the reservoir is 95% to 100% and/or between 85 to 95% and/or between 20 to 85% empty.

In some embodiments, disengaging 118 a drug delivery device from a subject may include retracting a needle. For example retracting a needle may include moving the needle with respect to a stationary housing and/or lengthening the housing to cover the tip of the needle.

In some embodiments, the device may sense disengaging 104b. Upon sensing disengaging 104b, discharging 111 may be stopped 119a. For example stopping 119a discharging 111 may include stopping 119a a pump and/or an actuator and/or a motor. Stopping optionally may preserve a power source for reuse. Alternatively or additionally, stopping 119a may include nullifying a working indicator 108b. Alternatively or additionally, stopping 119a may include locking the device to prevent restarting. In some embodiments the device may have a reset switch to unlock the device. The reset switch may be hidden and/or protected from user activation. Alternatively the reset switch may be available to the user. For example, after the device is locked, activating the reset switch may be cause the device to return to the unactivated and/or initial and/or unlocked state. Optionally there may be a warning and/or time delay before returning to the unactivated and/or initial and/or unlocked state.

In some embodiments, the operator indicator indicates 108c that it is safe to remove the device. For example, an operator who sees the safe to remove indication 108c may remove 122 the device from the subject. Optionally, a timer and/or indicator may warn the user and/or a supervisor if the device is not removed within a reasonable time period for example ranging between 1 second to 1 min and/or 1 to 3 minutes after injection is completed.

In some embodiments, at the end of discharge and/or after disengaging, the second indicator may indicate that the reservoir is fully discharged 125c. Optionally, when the device disengages a needle may retract. The retraction may be discernible from the second indicator. Alternatively or additionally retraction may not be discernible from the second indicator. In some embodiments, from the second indicator it may be difficult and/or ambiguous to discern if the injector can be safely removed and/or if the injector is still engaged to the subject.

In some embodiments, when a device is activated, self check 106 may include, for example, checking battery condition and/or motor condition and/or a position of a part (for example a plunger) and/or a check of stored information, for example a Not-activated flag in software and/or a check sum to verify software. If the self check comes out OK, then the operator indicator will optionally indicate 108b that it is ready for engagement to a subject. If there is a fault in self check 106, then the injector optionally goes into an error state 124d.

In some embodiments, there will be a time check for certain actions. For example after the indicating 108b that the device is ready the system may wait for the operator to engage 110 the device to a subject. Optionally, the system will keep checking the time and sensing 104a whether the device is engaged 110. If the time period ends without engagement 110, then the system optionally goes to an error state 124d and/or indicates 108d that an error has occurred. If the device senses 104a engagement 110 before the end of the time period, then the system optionally enters discharge stage 124b. For example, for a system where a operator is given an inactivated device and/or activates the device before use, the engaging wait time before indicating 108d an error may range between 30 sec. to 2 minutes and/or between 2 to 5 min and/or between 5 to 10 minutes and/or between 10 and 30 minutes. Alternatively or additionally a device may have a programmable engaging timer. For example, a device may be made to be given to an operator by a medical professional in an activated state. The device may wait a certain time period (for example ranging from one hour to 6 hours and/or from 6 hours to two days) and alert the operator (for example via the operator indicator and/or by another indicator) that the time to take his medicine has come (for example via a light indicator and/or an audio alarm and/or a cellular message). Then the device may optionally wait to be engaged. For example the device may wait a time period ranging between 30 sec. to 2 minutes and/or between 2 to 5 min and/or between 5 to 10 minutes and/or between 10 and 30 minutes and/or between 30 minutes to two hours. If the device is not engaged by the end of the wait period it may indicate an error (for example error indicator 108d).

In some embodiments, error indicator 108d may include a coded message associated with the device. For example, a LED may glow red and/or blink red. Alternatively or additionally, there may be an auditory indicator and/or a cellular message may be sent. For example the message may be sent to the operator and/or to a supervisor and/or a medical professional. Optionally a cellular message may include details of the status of the device. Optionally one or more messages may be sent to one or more recipients. Optionally a message may be tailored to the recipient. For example the message may be sent to an operator saying "drug delivery fault consult your doctor" whereas a message may be sent to a doctor with details of the error (whether any medicine was administered, how long and what time did the error occur etc.).

In some embodiments, when a fault occurs the device may be locked to prevent use of the device against instructions. Alternatively or additionally there may be a warning period and/or a warning indicator. If corrective action is not taken during the warning period the device may be locked. Alternatively or additionally, the device may remain usable when an error occurs and/or may lock due to certain errors and remain usable when there are other errors. Locking may be permanent and/or reversible (reversing the locking may be available to the operator and/or only to a medical professional). For example, for a device with an experienced operator (for example an insulin pump) the indications and/or options for the operator may be more complex and include more options and/or more reversibility. For example, for a device for inexperienced operators and/or more limited operators (for example an injector for use by a cancer patient and/or a geriatric patient) the errors may be stricter, the instructions simpler and/or the options more limited and/or the waiting times shorter.

In some embodiments, discharge stage 124b may have a time limit. For example, if discharging does not finish 116 within a determined time up 114 period, the device may go into an error state 124d. For example, the device may go into an time out error if the motor is not properly connected to the plunger. In such a case, without a time out error, the system may never discharge and/or discharge may never finish 116. Alternatively or additionally, if the system disengages before a determined minimum time period, the system may go into error state 124d. For example, a sub-minimum time error may occur when there is a blockage in a fluid path and/or the resistance to movement of the plunger rises high enough to cause the system to prematurely disengage 118. The minimal discharge time period and/or maximum time period 114 may vary, for example, minimal injection time and/or a minimal travel distance of the plunger may be determined according to the minimal drug volume of the filled reservoir and/or approve for a treatment. If time window or plunger movement less than a validated full dose, an alarm will optionally be activated. If on the time and/or with longer plunger travel distance is longer the injection may in some embodiments be treated as proper. If the time and/or plunger movement is beyond a maximum an error state and/or alarm may be activated. The threshold values may additionally depend on for example the consequences of an under-dose, the consequences of a mistaken missed delivery, the level of supervision, the expected variability of the discharge time, the physical condition of the operator, the mental condition of the operator and/or the experience of the operator (for example the likelihood to recognize and correct errors themselves). For example, the minimal discharge time period may range between 0 to 20% of the expected time period and/or between 20 to 50% and/or between 50 to 80% of the expected discharge period. For example, the maximum time period 114 may range between 100 to 120% of the expected time period and/or between 120 to 150% and/or between 150 to 200% of the expected discharge period and/or between 200 to 500% of the expected discharge period. The expected time period for discharge may vary for example with the viscosity and/or volume of the drug. For high viscosity and/or high volume of drug the expected injection time may increase.

In some embodiments, when the device enters an error state 124d, the system may be stopped. For example, stopping in an error state 124d may include some or all of the options mentioned above with respect to stopping after successful discharging 124b. In the error state 124d the operator may trigger a safety release 120. When the safety release is activated the device optionally stops 119b and/or locks the device (for example including actions like stopping 119a). After activating the safety release 120 a safety release indicator 121 may be activated. Optionally the user may remove 122 the injector. Optionally, the triggering safety release retracts a needle and/or causes display of a safety release indicator. For example the safety release indicator may indicate that it is safe to remove 122 the device (e.g. because the needle has been retracted). Alternatively or additionally, the safety release indicator may indicate that discharge 124b did not complete successfully and/or a supervisor should be consulted.

States of a Drug Delivery Device

FIG. 2 is a state diagram illustrating stages of operation of a drug delivery device in accordance with an embodiment of the current invention. In some embodiments a drug delivery device may have multiple stages of operation and/or states. An output device optionally conveys a first indicator (referred to herein as an operator indicator) of stages of operation of the device and/or of operational instructions. Optionally the output device may convey a coded indicator. Some embodiments may include second indicator assembly. For example the second indicator may present a status of the device and/or a stage of operation. In some embodiments, the operational indicator may be configured to attract the attention of the operator of the device. The second indicator may include details not conveyed in the operational indicator and/or the second indicator may be conveyed at times when the operator indicator is not being conveyed. For example the operator indicator may be an active indicator that requires power and/or operation of the device and/or the second indicator may be a passive indicator that can be used even when the device is powered down and/or not functioning.

In some embodiments, an operator of a drug delivery device may prepare 102 the device, engage 110 the device to a subject, wait 209 while the device delivers the drug, remove 122 the device from the subject and/or contacts a supervisor 223 for example for further instructions, for example in the case of a malfunction. An operator indicator is optionally configured to give clear and/or unambiguous indication of when the operator should perform one, some and/or all of the operations. In some embodiments, when the device is off 224 the indicator may null 208e indicating that the for example that the operator should activate the device.

In some embodiments, when the device is activated 124a and/or functioning properly the operator indicator may indicate 208a that the device is ready for engaging 110, for example by a blinking and/or glowing blue light. The ready to engage indicator 208a optionally reassures some users that the device is working properly. For example, this may increase the probability that an operator will successfully use the device. Alternatively or additionally, in some cases a self test will reveal a defect and/or convey an error indicator before the user engages the device. The user may be saved potential pain, inconvenience, risk and uncertainty associated with unsuccessful use of the device.

In some embodiments, when the device is engaged 124b and/or properly discharging the drug, the operator indicator may indicate that the device is working 208b and/or that the operator should wait 209, for example by a blinking green light.

In some embodiments, after successfully delivery and/or disengagement 124c the operator indicator may indicate 208c that it is safe to remove 122 the device. In some embodiments when a malfunction 124d occurs, the operator indicator may convey an error indicator 208d, for example a red glowing light, indicating for example that the user should activate the safety needle release and/or remove the device and/or contact 223 a supervisor.

In some embodiments, a drug delivery device may include a second state indicator assembly. For example, a drug delivery device may include a window through which an operator can see the status of the drug reservoir and/or its contents (payload). In some embodiments a window showing a state of a payload and/or drug reservoir may give an ambiguous indicator of status for determining user actions. For example, the state a reservoir may be an ambiguous indicator of whether the device is ready for engaging to a subject. For example, the reservoir may remain full 225a in both the off and activated state. For example, in the discharging state, when the reservoir is partially full 225b in order to tell if the reservoir is really discharging a user may either discern movement of the plunger and/or changes in the payload over time. Judging changes over time in some embodiment and/or for some users may be difficult or unreliable. The difference between the engaged 124b and disengaged 124c statuses (which are recognized by differentiating between a partially full 225b reservoir and a fully deployed 225c reservoir) may be difficult to discern from the physical state of the reservoir.

In some embodiments, a reassuring working indicator 208b and/or the clear differentiation between the working indicator 208b during engaged state 124b when system is working properly and/or the error state 124d optionally reassures a user. For example, this may prevent mistaken use of the safety release and/or premature removal the device before completion of delivery. In some embodiments, clear differentiation of the operator indicators of the working engaged state 124b and disengaged state 124c may avoid removal 122 of the device before disengaging 118 and/or potential pain or risk of improper removal of a needle. In some embodiments, clear differentiation of the operator indicators of the working engaged state 124b and the disengaged state 124c may avoid removal 122 of the device before disengaging 118 and/or potential pain or risk of improper removal of a needle. In some embodiments clear differentiation of the operator indicators of the working engaged state 124b and the disengaged state 124c may avoid an operator not recognizing when discharge has successfully completed and/or avoid inconvenience of not removing the device and/or avoid unnecessary drain on supervisor resources to reassure the user and/or check when delivery ended properly.

In some embodiments, the payload status may be useful for judging how much drug has been discharged 225d. For example, a passive window for viewing a reservoir may facilitate determining the quantity of drug remaining in the reservoir and/or the reservoir status. The optionally window for viewing the reservoir may serve to check the quality (for example the color) of the payload. A passive window for viewing a reservoir optionally functions when the device is working, when the device is not working and/or when there is power and/or when there is no power.

In some embodiments, an operator indicator may include an active output device such as a light and/or a sound source.

In some embodiments, a sensor and/or a reusable power switch may be used to determine timing and/or order of changes of state of the device. Control of the device and/or operator indicators may be according to the output of the sensor and/or reusable power switch.

In some embodiments some and/or each stage of delivery may have an active and/or coded and/or distinctive status indicator for reassuring an operator that delivery is proceeding properly and/or to help the operator determine in a very simple way what he needs to do. Alternatively or additionally, a device may have one or more error state and/or active and/or coded and/or distinctive error indicators.

In some embodiments a delivery device may have multiple inactive states. For example a device may have an unactivated and/or preliminary state 224 and/or a successful delivery stopped state 124*c* and/or and error stopped 124*d* state. Optionally some or all of the inactive states may have a passive indicator that allows an operator and/or a supervisor (for example a medical professional and/or a caretaker) determines whether and/or how much medicine was discharged and/or whether delivery proceeded normally.

Schematic Diagram of a Drug Delivery Device

Figure 3A:
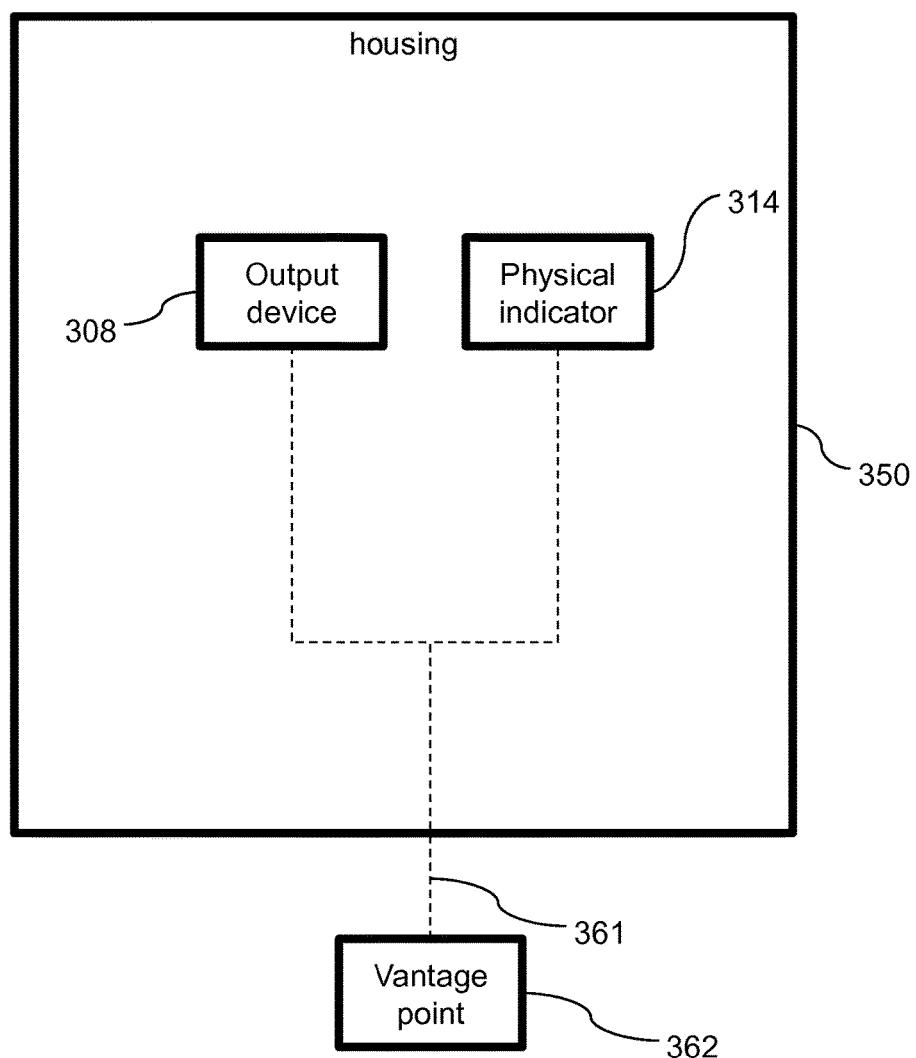
FIGS. 3A-3B are block diagrams a drug delivery device in accordance with an embodiment of the current invention.
Figure 3B:
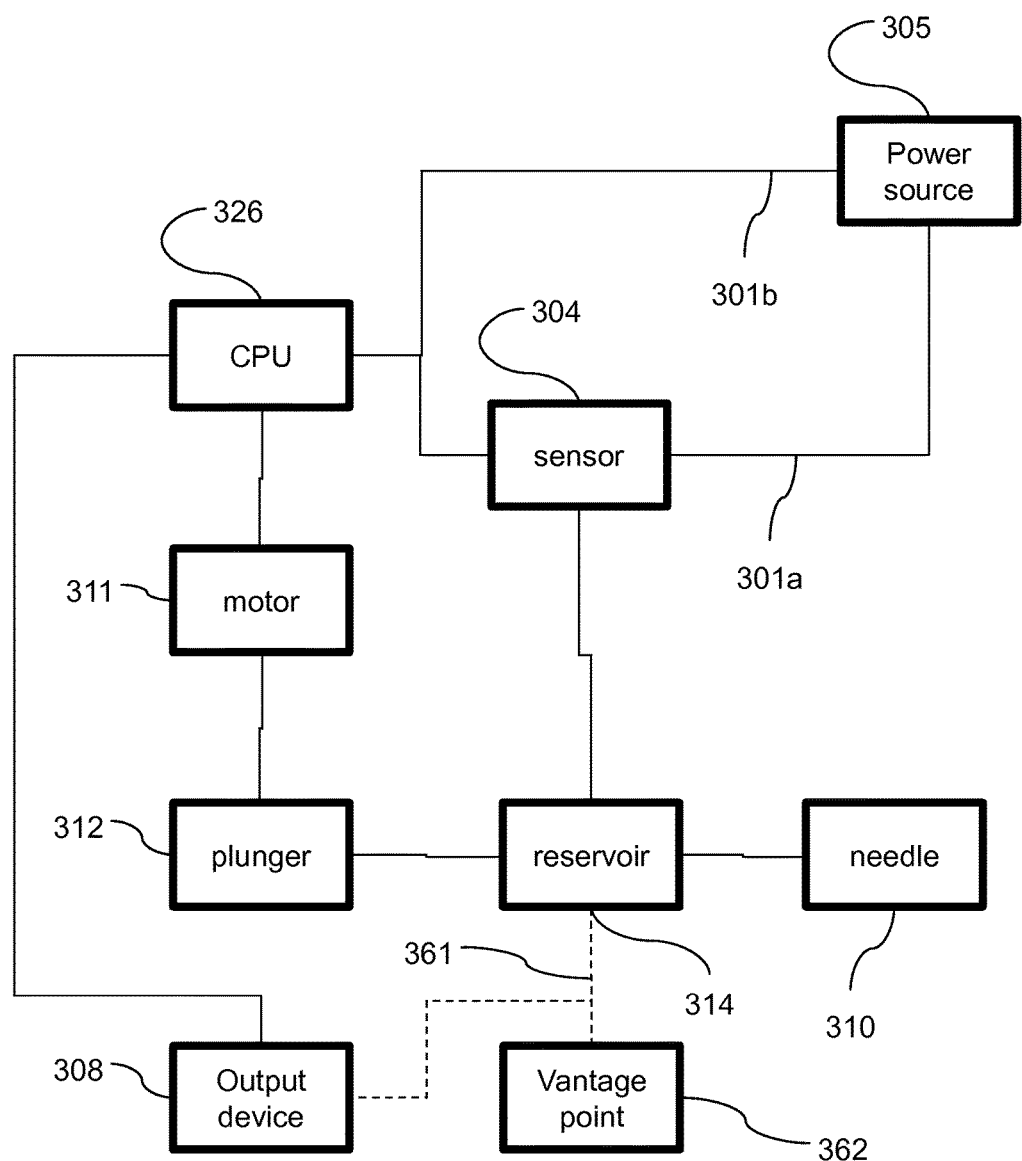

FIGS. 3A-3B are a block diagrams drug delivery devices with multiple status indicators in accordance with embodiments of the current invention. In some embodiments, multiple status indicators (for example a physical status indicator and a coded indicator) may be viewed through a shared optical path and/or may be visible in a single view. For example, a housing may define a shared optical path (for example a window). For example, the optical path may join a location outside the device to a physical status indicator such that a user can view the physical status indicator from outside the device. For example, the physical status indicator may include a space inside of a drug reservoir of the device. A coded light beam optionally is transmitted along said optical path. The coded light beam optionally includes coded status indicator visible to the user. The multiple status indicators (for example the space in the reservoir and/or the coded light beam) may be visible simultaneously and/or one indicator may surround the other and/or one indicator may obscure the other and/or one indicator may illuminate the other.

In some embodiments, a drug delivery device may include an operator indicator and/or a second indicator. Optionally the operator indicator may be configured to differentiate between conditions that require different actions of the operator. Optionally, the operator indicator may include a coded output configured for simple and/or easy to understand indication of states of the device that are pertinent to user actions and/or require user intervention. In some embodiments, the operator indicator may be more attractive and/or obvious than the second indicator. Optionally the second indicator may include a physical indicator.

In some embodiments, an operator indicator may be configured to attract the attention away from the second indicator. For example, the coded indicator may be designed to be brighter than the second indicator. Alternatively or additionally, light from the operator indicator may reflect off the physical indicator. Glare from the reflection may obscure viewing of the physical indicator. In some embodiments, the indicator may be selected (for example its color and/or strength and/or a blinking rate) to improve the visibility of the plunger and/or help recognize the quality of the reservoir contents. For example to the color of an indicator LED may be chosen to emphasize the difference between a proper color of the payload and an improper color.

In some embodiment, the operator indicator and second indicator may be designed to be viewed simultaneously. For example the operator indicator may illuminate the physical indicator. Alternatively or additionally the operator indicator may surround the second indicator on one, two, three and/or all sides thereof. Alternatively or additionally the physical indicator may surround the operator indicator on one, two, three and/or all sides thereof. Optionally all of the indication may be in a single location for example avoiding user confusion as to where to look.

In some embodiments, a reservoir may include a cartridge and/or a syringe and/or a soft walled vessel such as a bag. Optionally the reservoir is completely or partially transparent. For example, the reservoir may be partially and/or entirely constructed of a transparent and/or translucent material and/or may include a window for viewing the contents of the cartridge and/or an internal space thereof. Optionally, the reservoir may include a label. The label may be fully or partially transparent and/or translucent. The label may be viewable from the window (for example an operator and/or supervisor may be able to check that the correct drug has been inserted into the device).

Referring to FIG. 3A, in some embodiments, an output device 308 generating a coded indicator and/or a physical indicator 314 of device status are viewed by an operator from a vantage point 362 outside the device. Both output device 308 and/or physical indicator 314 are optionally seen along a single optical path 361 formed in a housing of the device 350. For example, when the coded indicator is activated, it may be visible in such a way that when the operator looks at physical indicator 314, he is also presented with coded indicator 308. The coded indicator may be configured to easily and/or obviously indicate to the user what action he currently should take in operating the device. For example, this may avoid the operator getting confused by an ambiguous status indication of physical indicator 314. Alternatively or additionally, the operator indicator may surround the physical indicator 314 on one or more sides and/or the physical indicator may surround the operator indicator and/or the two indicators may be viewable simultaneously and/or the operator indicator may obscure the physical indicator (for example glare produced by the operator indicator may make it difficult to see the physical indicator when the operator indicator is activated).

Referring to FIG. 3B, in some embodiments, a drug delivery device may include a patch injector and/or a pen injector and/or a stabilized injector and/or a medicine delivery patch and/or an inhaler and/or another drug delivery device. The device may be preloaded and/or may have a cartridge that is inserted by the operator of the device and/or by a supervisor (for example a medical practitioner and/or a pharmacist).

In some embodiments, a drug delivery device may include multiple power circuits. For example a first power circuit 301*a* may be controlled by a power switch 304. Power switch 304 may initially isolate a power source 305 from a pumping sub-system and/or an indicator 308. In some embodiments, power switch 304 may be toggled by an operator action to activate the device (for example by unpacking the device). After the system is activated, power switch 304 may optionally function as a sensor for determining a stage and/or state of the device. For example, power switch 304 may be toggled by movements of a needle and/or a reservoir of the device.

In some embodiments, after the system is activated, a processor 326 may control various components of the system. For example, processor 326 may send commands to operator indicator 308. For example, indicator 308 may indicate a stage and/or status of the device to an operator via coded output. Optionally, processor 326 may control discharge of a drug. For example, when a needle is engaged to a subject, processor 326 may send commands and/or electrical power to a motor 311 driving a plunger 312 to discharge the drug from a reservoir 314 through the needle 310 into the subject.

In some embodiments, after activation of the system, processor 326 may be responsive to signals from a sensor. Optionally, after activation, power switch 304 may be toggled by actions of the device while processor 326 receives power over circuit 301b. For example, power switch 304 may be toggled by movements of reservoir 314 and/or needle 310. Optionally, processor 326 may track the state of the device and/or issue commands based on the order and/or timing of toggling of switch 304 and/or based on the status of switch 304 and/or other sensors.

In some embodiments, control of various sub-systems may be based on direct connections to one or more sensors. Optionally the device may lack a central processor.

In some embodiments, motor 311 and/or output device 308 may be directly connected to a power switch. For example, when needle 310 is engaged to a subject, switch 304 is toggled on and/or motor 311 is optionally turned on and/or output device 308 is activated producing a working indicator. Optionally motor 311 drives a plunger 312 discharging a drug. When needle 310 is disengaged from the subject, switch 304 is optionally toggled off and/or motor 311 is optionally turned off, stopping discharge of the drug and/or output device is turned off and/or switched to produce a second coded indication. For example the second coded indication may indicate that delivery has finished and/or that it is safe to remove the delivery device.

Exemplary Drug Delivery Device with Redundant Indicators

Figure 4A:
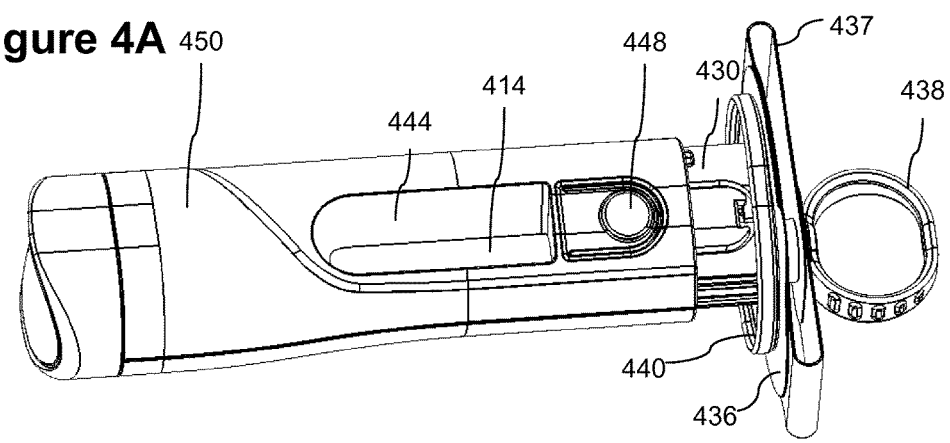
FIGS. 4A-4J are various views of a two sensor drug delivery device in accordance with an embodiment of the current invention.

FIG. 4A is a perspective external view of a multistage drug delivery device in an unactivated state in accordance with an embodiment of the current invention. In some embodiments, an operator indicator, for example an active output device such as a light and/or a sound source, may supply reassuring feedback when the device is functioning properly. An alternative indicator (for example a physical indicator) may inform the user of the status of delivery when the device is not active. For example, a passive sign and/or an optical path formed in the housing to view a reservoir and/or a state of the reservoir may make it possible as ascertain whether and/or how much medicine was discharged and/or whether the device has been used and/or whether the device went through an error state. In some embodiments a drug delivery device may include a written output (for example displayed on a view screen) and/or a verbal output (for example a synthesized voice produced by, for example, a voice synthesizer and/or a speaker).

In some embodiments, a physical indicator, for example drug reservoir 414, is optionally visible through a window 444 in a housing 450 of the device. Optionally, in the unactivated state, reservoir 414 is not illuminated. For example, before activating the device an operator and/or a supervisor may be able to look into the reservoir and determine the state of the contents; for example if the reservoir is properly filled, if the contents are the proper color etc. In some embodiments, window 444 may include an opening in the side of housing 450. The opening may be covered with a transparent and/or translucent pane and/or covering (for example glass and/or plastic). Alternatively or additionally, the opening may be uncovered and/or covered with a grating. Alternatively or additionally, the window and/or reservoir and/or label may include a reflective and/or fluorescent material. For example, the operator indicator may include an ultraviolet light and/or the window may have a fluorescent coating. When the ultraviolet light hits the coating, the window pane may glow and/or obscure the view of the reservoir.

In some embodiments a power switch or generator 403a and/or another switch 403b (see for example FIG. 4J) are repeatedly toggled by various components of the system as the drug distribution procedure proceeds. For example, pulling away a handle 438 and/or a protective cover 437 toggles a power switch or generator 403a and/or activates the device. Handle 438 is optionally connected to protective cover 437. The order and timing of the toggling are optionally used to distinguish and/or control stages of operation of the device and/or or to control an operator status indicator (for example a coded light signal) of the device. For example in the unactivated state, power switch or generator 403a isolates a power supply 405 from the power consuming components of the device. In the unactivated state, the operator status indicator is optionally not activated. For example, when handle 438 is attached to the device and/or the operator status indicator is not illuminated, the operator knows that the device has not yet been activated.

Figure 4B:
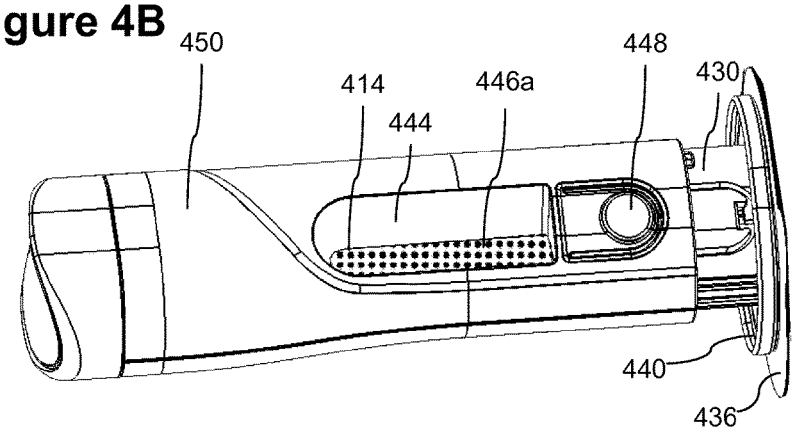

FIG. 4B is a perspective view of a drug delivery device in an activated state in accordance with an embodiment of the current invention. In some embodiments, in the activated state, reservoir 414 and/or window 444 are illuminated by a coded operator indicator light 446a (operator indicator light 446a is represented in FIG. 4B by the diamonds visible in window 444). For example, the activated stage indicator light 446a may be a constant blue illumination of the reservoir. Optionally, indicator light 446a may be more obvious than the physical state of reservoir 414 and/or may obscure the physical state of reservoir 414. For example, when an operator (who may be inexperienced) looks through window 444 during the activated stage, he immediately sees the obvious blue light. In some embodiments, an operator indicator (for example indicator 446a) may be visible throughout an optical path (for example window 444). Alternatively or additionally, the operator indicator may be visible in a part of the window and/or surrounding the window and/or outside of the window.

For example, handle 438 and/or protective cover 437 have been pulled away activating the device. Optionally, removing cover 437 uncovers an adhesive layer 436 covering and/or a skin contact member 440. For example, in the activated state, skin contact member 440 may be extended by a sleeve 430 past a needle tip.

Figure 4C:
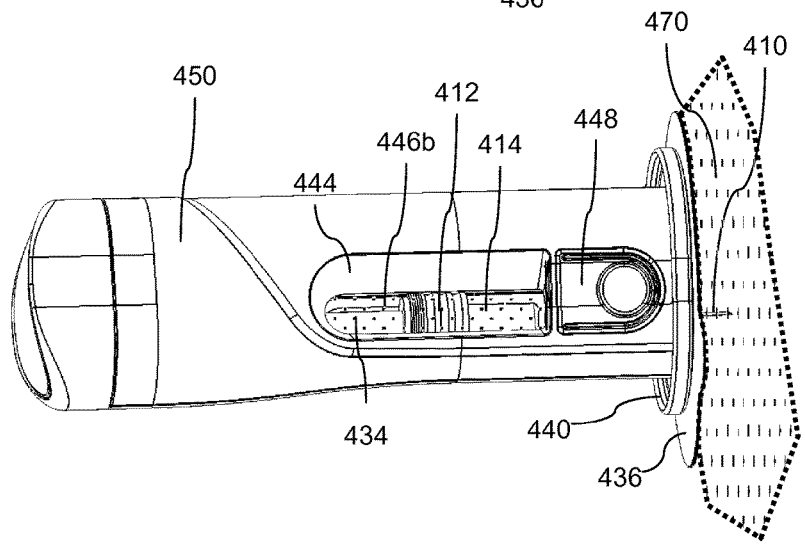

FIG. 4C is a perspective view of a drug delivery device in a discharging state in accordance with an embodiment of the current invention. In some embodiments, in response to sensor output, a motor may start to drive a plunger 412 and/or to discharge the drug and/or a coded discharging indicator may be initiated. In the discharging state an operator may optionally see plunger 412 as it passes along reservoir 414. In some embodiments, in the activated state, reservoir 414 and/or window 444 are illuminated by coded activated indicator light 446b. For example, the discharging stage indicator light 446b may be a blinking green illumination of the reservoir. Optionally, indicator light 446b may be more obvious than the physical state of reservoir 414 and/or may obscure the physical state of reservoir 414. For example, when an operator (who may be inexperienced) looks window 444 during the discharging stage, he sees that obvious green blinking light. In some embodiments, indicator light 446b may reassure the operator that the device is operating properly and/or will avoid the operator getting confused trying to understand the state of the device from the appearance of reservoir 414.

In some embodiments, the operator indicator may blink at a constant rate as long as the device is working properly and/or during the discharge stage. Alternatively or additionally, the rate of blinking may change over time. For example, the rate of blinking may increase and/or decrease over time. Alternatively or additionally, the rate of blinking may indicate a condition; for example the fill state of the reservoir (for example, solid green when the reservoir is full, slow blinking as the drug is discharged and/or faster blinking as the reservoir is further emptied and/or solid off when the reservoir is empty).

In some embodiments, while the device is in the activated state, an operator pushes skin contact member 440 against the skin 470 of a subject. Pressure optionally collapses sleeve 430 and/or shortens housing 450. Optionally, shortening housing 450 exposes the tip of needle 410. For example, needle 410 may penetrate the skin 470 of a subject. A sensor (for example the power switch of the device) optionally senses the collapse of sleeve 430. The delivery device may enter the discharge stage in response to output of the sensor.

Figure 4D:
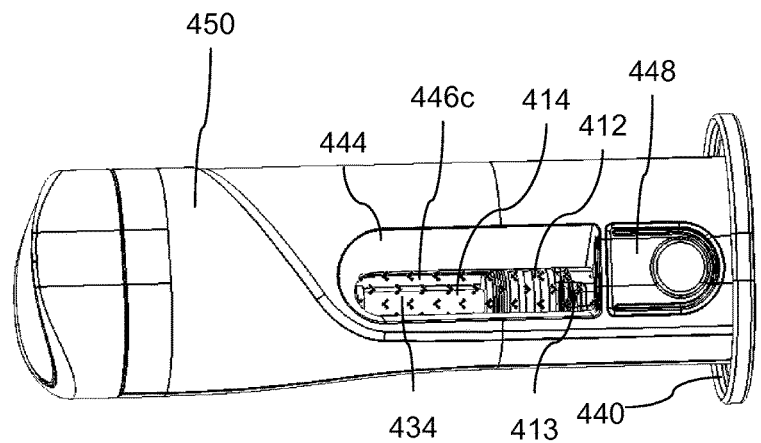

FIG. 4D is a perspective view of a drug delivery device in a stopped state in accordance with an embodiment of the current invention. For example, after successful drug delivery, needle 410 has been retracted into housing 450. In some embodiments, after successful delivery, reservoir 414 is illuminated by a coded activated indicator light 446*c*. For example, after successful delivery indicator and/or after retraction of needle 410 light 446*c* may be a constant green illumination of reservoir 414 and/or window 444. In some embodiments, once needle 410 has been retracted an operator may remove the device from the subject. After delivery and/or in the stopped state drug reservoir 414 is visible through a window 444. Optionally, the inside of reservoir 414 is visible through window 444. For example, in FIG. 4C, plunger 412 is shown having moved all the way to the distal end of reservoir 414 indicating that substantially all of the drug has been discharged. The reservoir optionally remains visible whether or not indicator 446*a*-446*d* is lit. For example, the operator and/or a supervisor can see whether the discharge completed and/or whether or not the electrical system of the device is working (for example after the power supply has been exhausted). Optionally, there may be a physical indicator of needle retraction. For example, the front end of the reservoir 413 (which for example may not be visible in the optical path including window 444 before needle 410 is retracted, but may move into the optical path when needle 410 is retracted) may have a color coded indicator strip (for example a green band) which becomes visible in window 444 when needle 410 is retracted.

Figure 4E:
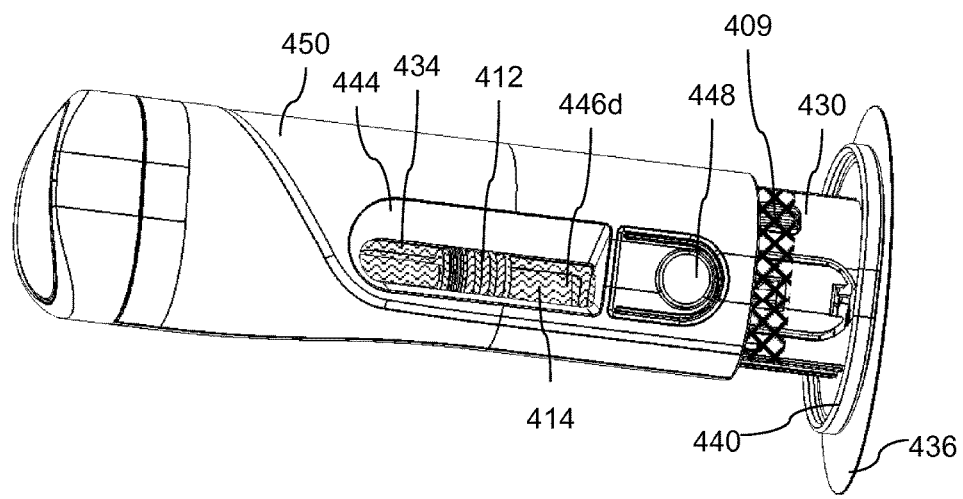

FIG. 4E is a perspective view of a drug delivery device in an error state after safety release in accordance with an embodiment of the current invention. For example, when an error occurs after activation of the device, an error indicator 446*d* (for example a red light) may be displayed. Optionally, upon seeing error indicator 446*d* an operator pushes a safety release button 448. Optionally, safety release button 448 releases sleeve 430 and/or skin contact member 440 to extend outward past needle 410. For example extending sleeve 430 may retract needle 410 from the subject to behind skin contact member 440. Extension of sleeve 430 in the safety release state (for example as illustrated in FIG. 4E) is optionally further than extension in the activated state (for example as illustrated in FIG. 4B). A safety release indicator strip 409 may be visible after safety release. For example indicator strip 409 may indicate that the safety release has been activated and/or that discharge may have been aborted and/or that needle 410 has been retracted by the safety release and/or that the device may be safely removed from the subject. For example, in FIG. 4C, plunger 412 is visible through window 444. Plunger 412 is still located near the middle of reservoir 414 indicating that not all of the drug has been discharged. The reservoir optionally remains visible whether or not indicator 446*a*-446*d* is lit. For example, the operator and/or a supervisor who can see whether the discharge completed whether or not the electrical system of the device is working (for example after the power supply has been exhausted).

Figure 4F:
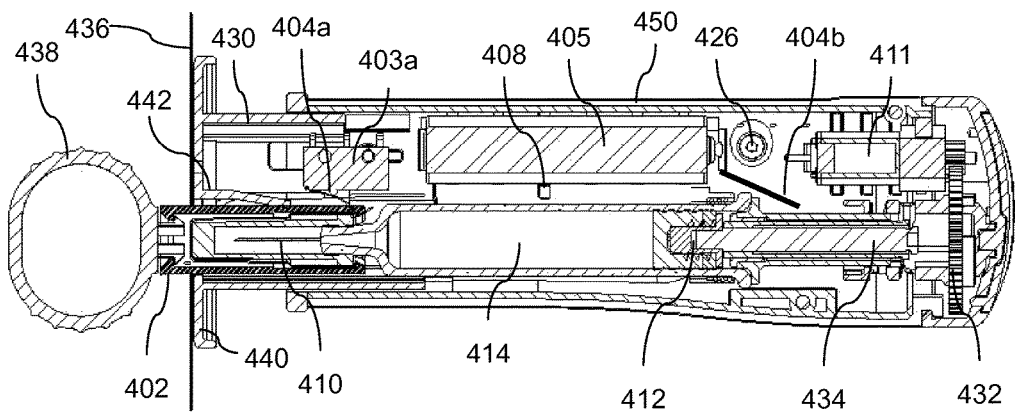

FIG. 4F is a cutaway viewing illustrating internal parts of a drug delivery device in an unactivated state in accordance with an embodiment of the current invention. Optionally, a drug delivery device may in include an output device (for example a light emitting diode LED 408). LED 408 may generate a coded indicator for example operator indicators 446*a*-446*d*. In some embodiments LED 408 may be directly visible to a user (for example through window 444 and/or through reservoir 414). Alternatively or additionally, LED 408 may be obscured by the walls of housing 450 and/or the user may only see secondary light (for example reflected and/or refracted and/or induced) from LED 408.

In some embodiments, a drug delivery device may include two sensor switches 403*a* and 403*b*. Optionally each switch 403*a* and 403*b* (for example as illustrated in FIG. 4J) includes a respective sensor arm 404*a* and 404*b*. In the unactivated state, power source 405 (for example a battery) is optionally isolated from the active components of the system (for example a motor 411 and/or a processor 426 and/or an output device, for example LED 408). For example, in the embodiment of FIG. 4F, power source 405 is optionally isolated from the active components of the system by power switch 403*a* which is in a disconnect configuration. Switch 403*a* optionally remains in the disconnect configuration as long as sensor arm 404*a* is deflected towards the body of switch 403*a*. In some embodiments, in the unactivated state and/or while sensor arm 404*a* remains deflected towards the body of switch 403*a*, substantially no power is drained from power source 405 and/or the delivery device consumes substantially no power. In some embodiments, sensor arm 404*a* may be held deflected toward the body of switch 403*a* by a protective needle cover 402.

Figure 4G:
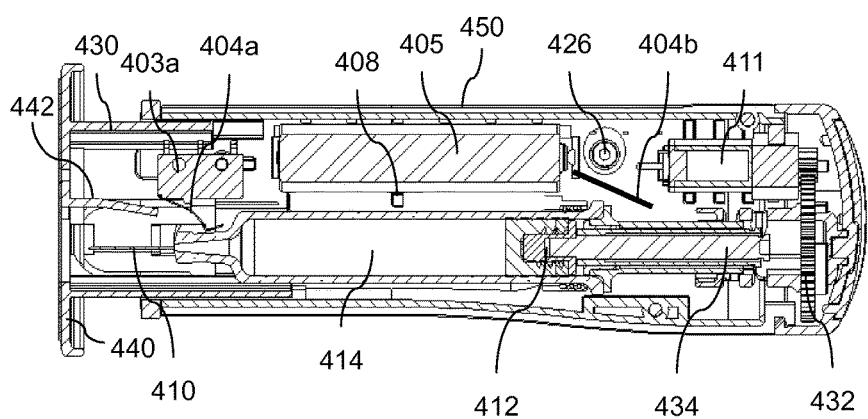

FIG. 4G is a cutaway view illustrating internal parts of a drug delivery device in an activated state in accordance with an embodiment of the current invention. In some embodiments, when processor 426 is powered up from the unactivated state, processor 426 performs a device self test and/or activates a second power circuit. If the self test is successful, processor 426 connects LED 408 to power source 405 and/or commands LED 408 to indicate that the device is activated and/or ready for engagement.

In some embodiments, switch 403*a* is toggled to a connecting state and/or connects power source 405 to processor 426. For example, switch 403*a* may be toggled to a connecting state when an operator removes a protective cover 402. Particularly, in some embodiments, when cover 402 is removed sensor arm 404*a* is released and/or moves away from switch 403*a*, toggling switch 403*a* to the connected configuration.

Figure 4H:
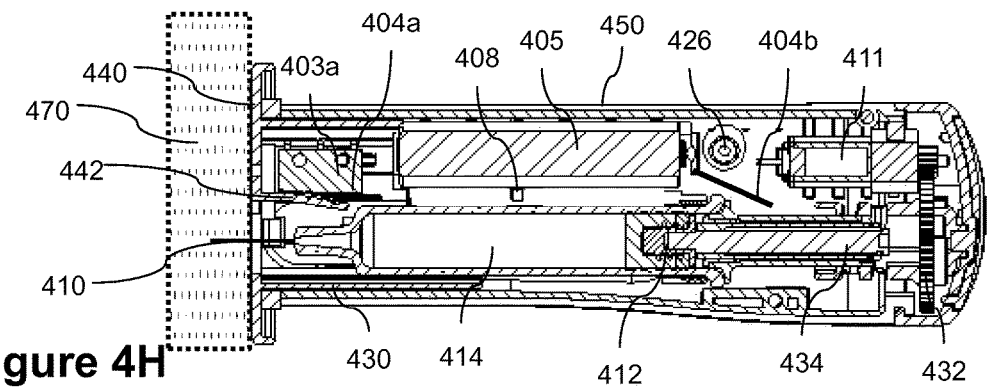

FIG. 4H is a cutaway viewing illustrating internal parts of a drug delivery device in an engaged and/or discharging state in accordance with an embodiment of the current invention. Optionally, switch 403*a* is toggled when the device is engaged to a subject; for example when needle 410 extends into skin 470 of the subject. When the device in the activated state, the device may respond to toggling of switch 403a by entering a discharge state. Entering a discharge state may include for example initiating discharge of the drug and/or indicating that discharge has started (for example via a coded indicator from LED 408).

In some embodiments, switch 403a may be toggled by movement of skin contact member 440 with respect to housing 450. For example, an operator may hold housing 450 and/or press skin contact member 440 against skin 470 of a subject until sleeve 430 collapses and/or slides into housing 450. Optionally as sleeve 430 moves with respect to housing 450, it contacts arm 404a and/or toggles switch 403a. For example as sleeve 430 collapses a portion 442 of contact member 440 presses against arm 404a toggling switch 403a. As sleeve 430 slides into housing 450, needle 410 is optionally exposed and/or inserted into skin 470. Optionally, after the activated stage, when switch 403a is toggled to a disconnect state, the second power circuit continues to supply power from power source 405 to processor 426 and/or other elements of the device. Optionally, processor 426 may include a timer and/or a real time clock. In some embodiments, processor 426 may track elapsed time between events and/or issue alerts and/or error messages and/or place the device into an error state when an expected event does not occur in the proper time period and/or when events occur in an improper time period.

In some embodiments, discharge may be driven by a motor 411. For example, motor 411 may drive a transmission 432. Optionally transmission 432 drives an extending screw 434 and/or plunger 412.

Figure 4I:
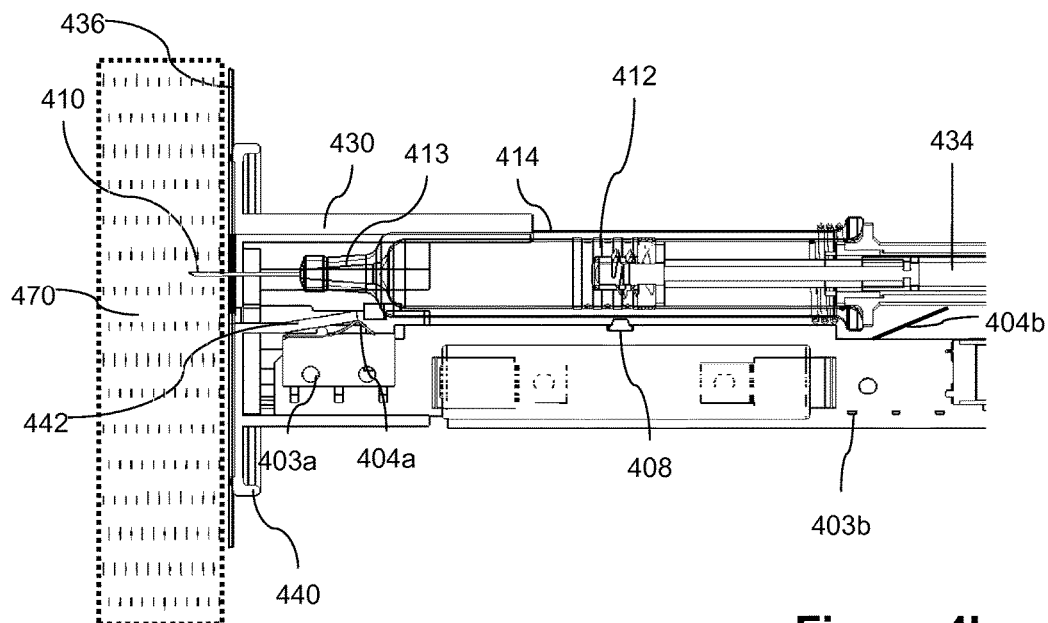
Figure 4J:
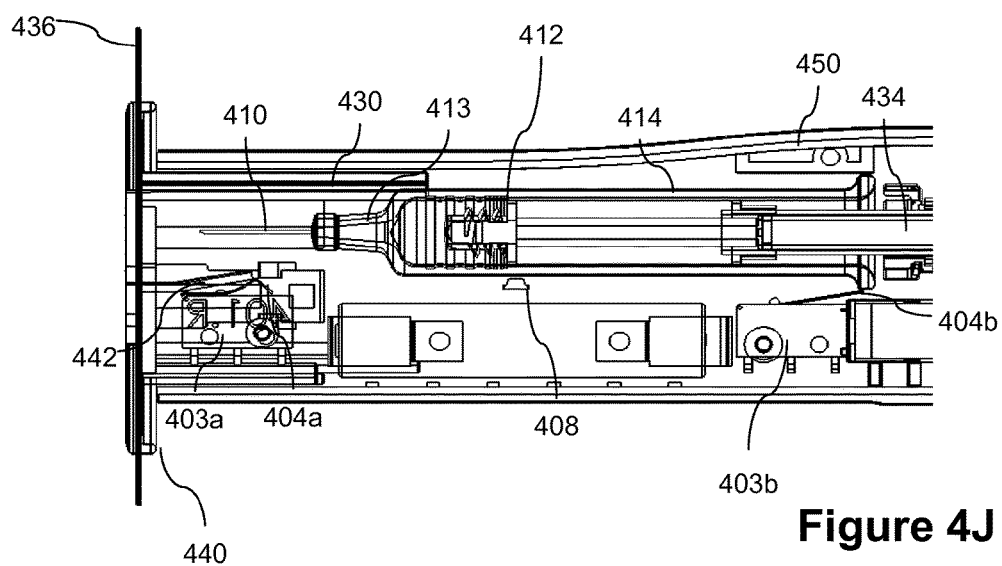

FIGS. 4I-4J illustrate toggling a switch by retraction of reservoir 414 and/or needle 410 in accordance with an embodiment of the current invention. In some embodiments, a drug distribution device may have two sensors 403a-403b. In some embodiments, according to the order and/or timing toggling of first and/or second switches 403a-403b, the device differentiates between retraction due to a operator releasing a safety release (for example as illustrated in FIG. 4E and automatic retraction and retraction for example as illustrated in FIG. 4I (for example automatic retraction may be due to completion of delivery and/or a obstruction of a fluid path). In some embodiments, according to the order and/or timing toggling of first and second switches 403a-403b, the device differentiates between premature retraction (for example due to obstruction of a fluid path) and retraction at the end of delivery (as illustrated for example in FIG. 4J, where plunger 412 has reached the end of reservoir 414 and/or discharged the entire contents of reservoir 414). When the order and/or timing of toggling is proper, a successful completing indicator (for example indicator 446c) may be activated. When the order and/or timing of toggling is improper, an error indicator (for example indicator 446d) may be activated.

In some embodiments, second sensor arm 404b is distanced from second switch 403b before and/or during operation of a drug delivery device (for example in the engaged state as illustrated for example in FIG. 4I). Optionally, when needle 410 and/or reservoir 414 are retracted, reservoir 414 pushes arm 404b towards switch 403b toggling switch 403b (for example as illustrated in FIG. 4J) Depending on the order of previous operations and/or timing thereof, processor 426 optionally responds to toggling of sensor 403b as a sign of premature end to delivery and/or successful completion of delivery. Optionally processor 426 responds to toggling of sensor 403b by activating an appropriate state indicator and or by starting or stopping an appropriate device (for example stopping discharge and/or locking the injector).

In some embodiments, if the delay between the beginning of discharge and toggling switch 403b is less than 80% of the expected delivery time and/or less than 50% of the expected delivery time and/or less than 25% of the expected delivery time, it may be assumed that discharge did not go to completion. If the delay ranges for example between 80% to 120% and/or between 50% and 200% and/or between 25% and 400% then the discharging may be assumed to have gone to completion. For example, for The minimal discharge time period and/or maximum time period may vary, for example, according to the expected discharge time, the consequences of an under-dose, the consequences of a mistaken missed delivery, the level of supervision, the expected variability of the discharge time, the physical condition of the user, the mental condition of the user and/or the experience of the user (for example the likelihood to recognize and correct errors themselves).

In some embodiments, during automatic retraction reservoir 414 may toggle sensor 403b without affecting sensor 403a; whereas safety release from an engaged state (caused for example by a operator pushing safety release button 448) may cause extension of skin contact element 440 toggling sensor 403a without affecting sensor 403b.

Optional Illumination Points

Figure 5:
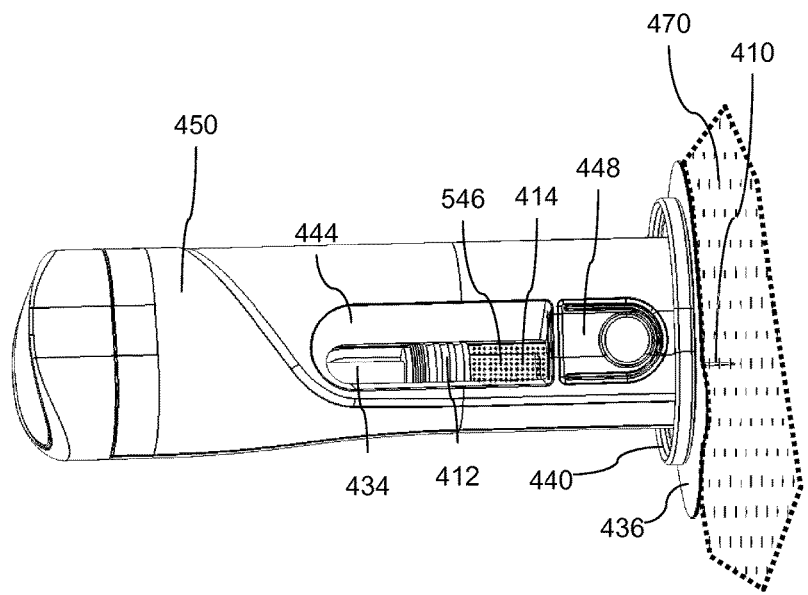
FIG. 5 is a perspective illustration of a drug delivery device wherein a coded indicator illuminates the contents of a reservoir in accordance with an embodiment of the current invention.
Figure 6:
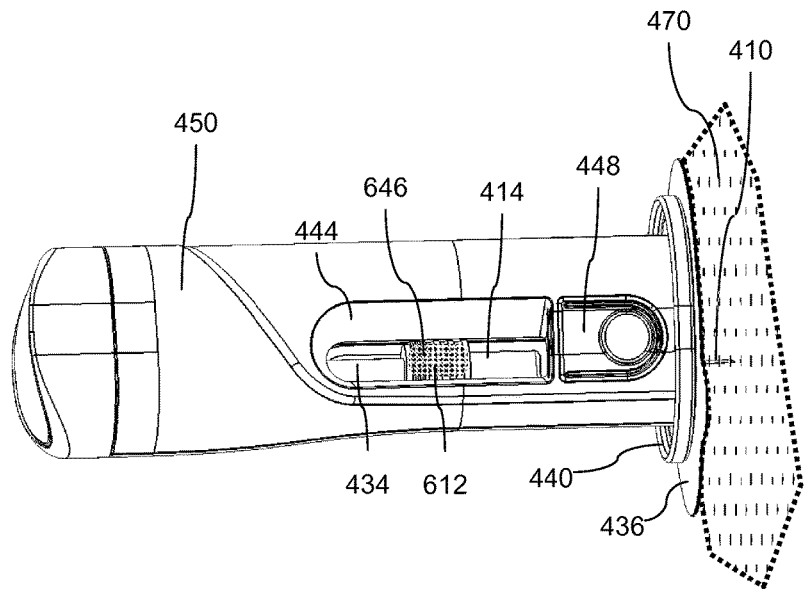
FIG. 6 is a perspective illustration of a drug delivery device wherein a coded indicator illuminates a component of a reservoir in accordance with an embodiment of the current invention.
Figure 7:
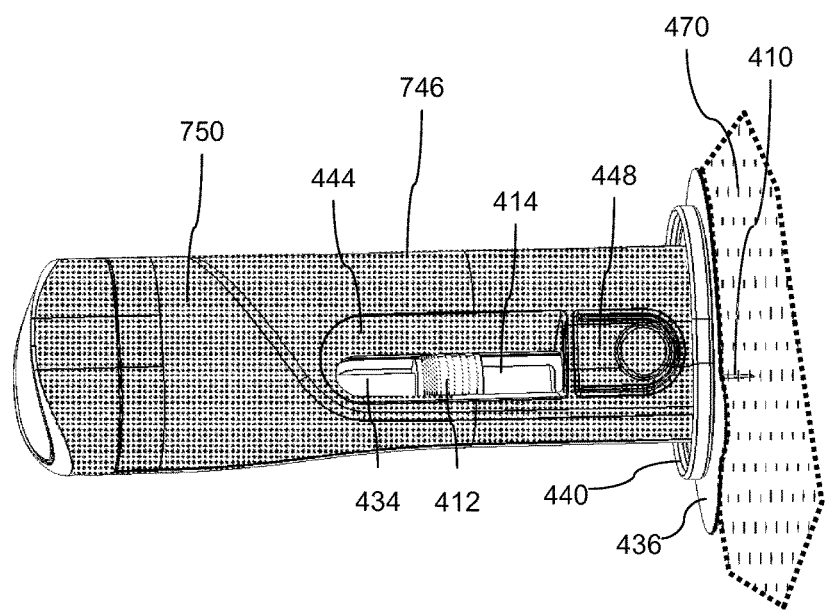
FIG. 7 is a perspective illustration of a drug delivery device wherein a coded indicator illuminates the housing around a reservoir in accordance with an embodiment of the current invention.

FIGS. 5-7 are external views of alternative illumination points in accordance with some embodiments of the current invention. For example as illustrated in FIG. 5, an operator indicator may illuminate the remaining drug in the reservoir. For example an operator indicator 546 may include light that is not directed toward along an optical path visible to the operator. The light may become visible along the optical path when it is dispersed and/or diffracted and/or reflected and/or transformed (for example by fluorescence) by the drug in the reservoir.

In some embodiments, for example, as illustrated in FIG. 6, an operator indicator 646 may be visible to the operator when it reflects of a component of the injector, for example a reflective plunger 612.

In some embodiments, for example, as illustrated in FIG. 7, a portion of a housing and/or an entire housing 750 may be translucent and/or transparent and/or fluorescent. An operator indicator 746 may optionally be visible in some and/or all of the housing. For example, operator indicator 746 may be visible in housing 750 surrounding a window 444.

Exemplary Dimensions of a Drug Delivery Device

In some embodiments the payload of a reservoir (for example a syringe) may include, for example between 0.5 and 2 ml and/or between 2 and 4 ml and/or between 4 and 5 ml of a drug and/or more. In some embodiments, the injector may discharge the entire payload as a single dose. A drug delivery device may include, for example, a pen injector, and/or an internally powered driver to drive the plunger and/or discharge the payload. For the sake of this application an internally powered injector driver may be defined as a drive mechanism powered by energy stored at least temporarily within the injector. Power may be stored in a power supply, for instance as chemical potential (for example a chemical that produces an expanding gas and/or a battery) and/or mechanical potential (for example stored in an elastic member and/or a spring and/or a pressurized gas). For example the driver may be designed to discharge the payload over a time period ranging between 20 and 120 seconds and/or between 120 and 600 seconds and/or longer.

In some embodiments, discharge may be driven by a driver. An internally powered driver may be powered by various mechanisms including for example a motor (including for example a DC motor, an actuator, a brushless motor) and/or a transmission including for example a telescoping assembly and/or a threaded element and/or a gear and/or a coupling and/or an elastic mechanism (for example a spring and/or a rubber band) and/or an expanding gas and/or a hydraulic actuator).

A drug delivery device in accordance with some embodiments of the current invention may include reservoir. For example a reservoir may include a medicine container and/or a standard type syringe. Optionally a standard type syringe may be preloaded with medicine using standard equipment and/or in an aseptic room. A preloaded standard type syringe may optionally include a proximal opening. A plunger may optionally seal the proximal opening and/or protect the sterility of the contents of the syringe. A sterile needle (for example a hollow needle) may optionally be connected to the syringe barrel. For example, the hollow of the needle may be in fluid communication with the interior of the barrel. The needle may optionally be rigidly attached to the distal end of the barrel. The sterility of all and/or part of the needle may for example be protected by a sterile cover. The sterile cover may remain on the needle when the syringe is supplied and/or installed into an injector. For example, the medicine container may optionally include a cylindrical barrel rigidly attached to a needle. Optionally, the long axes of the needle and barrel of the syringe may be parallel and/or coaxial. Optionally, the needle may be mounted on the distal end of the barrel. Optionally the needle point may be pointing in the distal direction. In some embodiments a plunger may slide axially along the inside of the barrel to discharge a medicine payload. For example, the medicine may be discharged through the hollow needle.

An aspect ratio of the base may be defined as the ratio of the length of the longest axis of the base to the shortest axis. Optionally the axis ratio may range between 1.5 to 2 and/or between 2 to 3 and/or greater than 3. In some embodiments, the height of the injector may range between half the length of the short axis of the base to the length of the short axis of the base and/or between the length of the short axis of the base to twice the length of the short axis of the base and/or greater than the twice length of the short axis of the base. The height of the injector may supply leverage for pivoting the adhesive off the skin of a patient after use.

In some embodiments, the force to insert the needle to the skin of a patient may range for example between 0.02 to 0.2 N and/or between 0.2 and 0.5 N. Optionally, the force required to inject the drug (for example the force on a syringe plunger) may range for example between 5 to 60 N. For example the force required to inject the drug may depend on the injection rate and/or the viscosity of the drug and/or the syringe geometry and/or the needle dimensions.

In some embodiments a needle protection mechanism may be triggered by a linear force greater than, for example, between 10 to 60 N.

For example, drug delivery device may include an autoinjector. The autoinjector may be activated by manually pushing with enough force to insert the needle. The device may then apply an injection force to inject a drug. Once the entire drug is injected and/or when there is an obstruction and/or occlusion, the injection force may rise until it passes a threshold triggering safeguarding of the needle and/or ending injection.

For example in the event of an occlusion and/or at the end of delivery, the linear force generated by the device may increase to the level of up to 60 N. A needle safeguarding mechanism (for example a needle retraction mechanism) may be sensitive to the force. For example mechanism may include a snap that gives way at 40 N returning the needle to the retracted position.

In some embodiments, the stress to inject a medicine and/or to trigger safeguarding of a needle may include a torque. For example, injection of medicine may be driven by a plunger. The plunger may optionally be driven by a threaded assembly, for example a threaded screw and/or teeth and/or a telescoping assembly. Optionally the pitch of the teeth and/or an associated screw may range for example between 0.5 and 2 mm. The diameter of the screw may range for example between 3 and 15 mm. The torque to power injection may range for example between 0.2 and 1.0 N*cm. The trigger torque (the torque at which the needle safeguarding is triggered) may range for example between to 0.5 to 2 and/or from 2 to 4 and/or from 4 to 10 N*cm.

In some embodiments a safety mechanism may include linear movement of the ranging between 5 to 15 mm. For example movement of the safety mechanism may include extension of a needle during insertion and/or retraction of the needle and/or extensions of a safety shield and/or retraction of a safety shield. Optionally a needle insertion length (for example the length of needle inserted into a patient) may range for example between 3 to 12 mm.

During injection, the linear movement of a plunger may range for example between 10-50 mm. The length of movement of the plunger may vary for example with the volume of medicine to be injected that may range for example between 0.5 to 3 ml.

In some embodiments, a safeguarding mechanism may be sensitive to a torque. For example, the needle may be retracted when the mechanism is exposed to a twisting moment. Optionally, discharge may be driven by a torque. For example the driver may apply torque to threaded element pushing a plunger. When the torque on the driver reaches a threshold value, the needle may be released and/or retracted and/or a needle shield may be deployed. Alternatively or additionally the trigger mechanism may require both a torque and a linear force. For example, requiring both a torque and a linear stress may prevent premature activation due to momentary friction.

In some embodiments a time of discharge may range may depend on the fill volume and/or viscosity For example the expected injection speeds may be Injection speed depend on viscosity, for example for viscosity ranging from 1 cp to 15 cp the expected injection rage may range between 30 to 40 sec/1 ml, for example for viscosity ranging from 15 cp to 60 cp the expected injection rate may range between 35 to 60 sec/ml for viscosity above 60 cp the expected injection rate may range between 53 to 67 sec/1 ml. The maximum and/or minimum expected injection time may for example be the maximum and/or minimum allowed fill volume divided by an injection rate. For example an expected time of discharge may range for example between 24 to 48 seconds (for example for between 0.8 and 1.2 ml of fluid having a viscosity ranging between 1 to 15 cp) and/or between 36 to 68 seconds (for example for between 1.2 and 1.7 ml of fluid having a viscosity ranging between 1 to 15 cp) and/or between 51 to 92 seconds (for example for between 1.7 and 2.3 ml of fluid having a viscosity between 1 to 15 cp) and/or between 70 to 150 seconds (for example for 2.0 to 2.5 ml of fluid having a viscosity of between 15 and 40 cp) and/or between 120 seconds and 3 minutes for larger volumes and/or viscosities.

In some embodiments the drug delivery device may be configured to operate independently and/or be handheld. For example, the device may have a weight ranging between 10 grams to 30 grams and/or between 30 grams to 150 grams and/or between 150 grams to 500 grams. Optionally the drug may be contained within the device. Optionally the fluid path of the drug from the reservoir to the injection needle may be within the device. Optionally the power supply may be within the device. Optionally the device may be operable with one hand.

It is expected that during the life of a patent maturing from this application many relevant technologies will be developed and the scope of the terms are intended to include all such new technologies a priori.

As used herein the term "about" refers to ±5%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device for delivering a drug from a reservoir comprising:
   a housing with a space shaped to hold the reservoir and a window adjacent the space; said housing defining an optical path from outside the device through the window to an interior of the reservoir such that a payload status of the reservoir can be discerned from a vantage point outside the device;
   a generator of a coded light signal, said generator positioned so that at least a portion of said coded light signal travels along said optical path wherein said interior of said reservoir and said coded light signal are visible along said optical path simultaneously and viewable from said vantage point through the window and reservoir to assess the pay load status of the reservoir such that the payload status of the reservoir can be discerned from the vantage point along the optical path and outside the device.

2. The device of claim 1, further comprising:
   a sensor directed toward said space for sensing the payload status of the reservoir and wherein said generator is responsive to output of said sensor.

3. The device of claim 1, further comprising:
   a processor receiving feedback from the device and said processor controlling said generator in accordance to said feedback.

4. The device of claim 3, wherein said processor is configured to generate a code for the coded light signal to indicate that said apparatus is functioning properly.

5. The device of claim 3, further comprising:
   a sensor located within the housing directed toward said space for sensing the payload status of the reservoir and feedback including an output of said sensor.

6. The device of claim 5, wherein said sensor includes a position sensor sensing a position of the reservoir.

7. The device of claim 3, further comprising: a position sensor operationally connected to said processor, said position sensor sensitive to a position of said reservoir, and said feedback including an output of said position sensor.

8. The device of claim 1, further comprising:
   a position sensor sensing a position of the reservoir and wherein said generator is responsive to output of said sensor.

9. The device of claim 1, wherein said generator is configured to generate said coded light signal to indicate that said device is functioning properly.

10. The device of claim 1, wherein said generator is configured for illuminating at least a portion of said reservoir with said coded light signal.

11. The device of claim 1, wherein said generator is configured for obscuring at least a portion of said reservoir with said coded light signal.

12. The device of claim 1, further comprising said reservoir at least partially filled with the drug.

13. The device of claim 1, wherein said generator generates the coded light signal in between 3 and 6 modes.

14. The device of claim 1, wherein said generator generates the coded light signal with three colors, a constant signal and a blinking signal.

15. A device for delivering a drug from a reservoir comprising:
- a drug reservoir including a transparent portion through which an interior of the du reservoir is visible such that a payload status of the drug reservoir can be discerned from a vantage point outside the device;
- a housing with a space shaped to hold the drug reservoir and a window adjacent the space, the housing defining an optical path from the vantage point outside the device through the window and the transparent portion of the drug reservoir to the interior of the reservoir; and
- a generator of a coded light signal, said generator positioned so that at least a portion of said coded light signal overlaps said transparent portion of the drug reservoir and window from said vantage point along the optical path and is viewable through the transparent portion, window, and drug reservoir to assess the payload status of the drug reservoir.

16. A method of indicting a status of a system for delivering a drug, the system including a housing with a space shaped to hold a reservoir for said drug and a window adjacent the space, the method comprising:
- exposing an internal portion of said reservoir to a vantage point outside the housing via an optical path, the optical path extending through the internal portion of the reservoir and the window adjacent the reservoir to the vantage point outside the housing;
- generating a coded light signal; and
- indicating a status of the system with said coded light signal transmitting said coded light signal along said optical path to said vantage point viewable simultaneously with the payload of the reservoir along said optical path through the window and reservoir to assess the payload status of the reservoir such that a payload status of the reservoir can be discerned from a vantage point along the optical path and outside the device.

17. The method of claim 16, further comprising:
illuminating said internal portion of said reservoir with said coded light signal.

18. The method of claim 16, further comprising:
reflecting a portion of said coded light signal from said reservoir.

* * * * *